(12) United States Patent
Bonde et al.

(10) Patent No.: US 7,883,884 B2
(45) Date of Patent: Feb. 8, 2011

(54) CONCEPT FOR SLURRY SEPARATION AND BIOGAS PRODUCTION

(75) Inventors: Torben Bonde, Egaa (DK); Lars Jorgen Pedersen, Hadsten (DK)

(73) Assignee: GFE Patent A/S, Loejstrup (DK)

( * ) Notice: Subject to any disclaimer, the term of this patent is extended or adjusted under 35 U.S.C. 154(b) by 970 days.

(21) Appl. No.: 10/362,128

(22) PCT Filed: Aug. 22, 2001

(86) PCT No.: PCT/DK01/00553

§ 371 (c)(1),
(2), (4) Date: Aug. 13, 2003

(87) PCT Pub. No.: WO02/15945

PCT Pub. Date: Feb. 28, 2002

(65) Prior Publication Data

US 2004/0025715 A1    Feb. 12, 2004

(30) Foreign Application Priority Data

Aug. 22, 2000  (DK) ............................... 2000 01246
Feb. 1, 2001   (DK) ............................... 2000 00171

(51) Int. Cl.
    C12N 7/04   (2006.01)
    C12N 1/00   (2006.01)
    A62D 3/02   (2007.01)
    C12P 1/00   (2006.01)
    A23L 1/00   (2006.01)

(52) U.S. Cl. ................... 435/236; 435/243; 435/262.5; 435/264; 435/267; 435/268; 99/484; 99/485

(58) Field of Classification Search .................. None
    See application file for complete search history.

(56) References Cited

U.S. PATENT DOCUMENTS 4,041,182 A    8/1977   Erickson et al.

(Continued)

FOREIGN PATENT DOCUMENTS

HU           181389 B     7/1983

(Continued)

OTHER PUBLICATIONS

Charles A. Gray and A. Paul Schwab "Phosphorus-Fixing Ability of High pH, High Calcium,Coal-Combustion, Waste Materials" Water, Air, and Soil Pollution 69: 309-320, 1993.*

(Continued)

Primary Examiner—Christopher R Tate
Assistant Examiner—Aaron J Kosar
(74) Attorney, Agent, or Firm—Iver P. Cooper

(57) ABSTRACT

The present invention concerns an anaerobic digestion of animal manures, energy crops and similar organic substrates. The process is capable of refining nutrients comprised in the digested biomass to fertilizers of commercial quality. The invention also provides a method for oprocessing animal carcasses or fractions thereof including meat and bone meal etc., with the objective of providing an alternative means for processing the organic waste material of animal origin while at the same time facilitating the production of fertilizers. The risk of spreading BSE prions or any other prions to animals or humans is thus substantially reduced if not eliminated. The biogas and slurry separation system according to the present invention is preferably integrated with the operations of animal husbandries into a total concept in which the internal and external performances of animal husbandries are optimised. The internal performances concern quality aspects related to the management of the animal houses and include industrial hygiene, animal welfare, gaseous and dust emissions and food safety. The external performances concern mainly energy production and emissions to the environment of nutrients and greenhouse gases and the sale of high quality food product.

107 Claims, 6 Drawing Sheets

U.S. PATENT DOCUMENTS

| | | | |
|---|---|---|---|
| 4,100,023 A | | 7/1978 | McDonald |
| 4,108,735 A | * | 8/1978 | Burcaw et al. ............... 203/7 |
| 4,329,428 A | | 5/1982 | Ghosh et al. |
| 4,579,654 A | | 4/1986 | Bremmer |
| 4,668,250 A | | 5/1987 | Drese |
| 4,750,454 A | | 6/1988 | Santina et al. |
| 4,942,049 A | * | 7/1990 | Schmid et al. ............. 426/329 |
| 4,997,486 A | | 3/1991 | Bolsing |
| 5,009,672 A | * | 4/1991 | Ruffo et al. .................. 44/593 |
| 5,071,559 A | | 12/1991 | Bleeker |
| 5,296,147 A | | 3/1994 | Koster et al. |
| 5,389,258 A | | 2/1995 | Smis et al. |
| 5,422,015 A | * | 6/1995 | Angell et al. .............. 588/257 |
| 5,494,587 A | | 2/1996 | Morlec et al. |
| 5,525,229 A | | 6/1996 | Shih |
| 5,593,590 A | * | 1/1997 | Steyskal .................... 210/603 |
| 5,616,163 A | | 4/1997 | Halfter |
| 5,656,059 A | | 8/1997 | Monster et al. |
| 5,670,047 A | | 9/1997 | Burke |
| 5,681,481 A | | 10/1997 | Christy et al. |
| 5,746,919 A | | 5/1998 | Dague et al. |
| 5,773,526 A | | 6/1998 | Van Dijk et al. |
| 5,782,950 A | * | 7/1998 | Kanitz et al. .................. 71/10 |
| 5,783,073 A | | 7/1998 | Christy et al. |
| 5,851,404 A | | 12/1998 | Christy et al. |
| 5,853,450 A | | 12/1998 | Burnham et al. |
| 5,863,434 A | | 1/1999 | Massé et al. |
| 5,948,275 A | * | 9/1999 | Djafer et al. ................ 210/762 |
| 6,071,418 A | | 6/2000 | Tai |
| 6,171,499 B1 | | 1/2001 | Bouchalat |
| 6,555,350 B2 | | 4/2003 | Ahring et al. |

FOREIGN PATENT DOCUMENTS

| | | | |
|---|---|---|---|
| HU | 61254 | | 12/1992 |
| HU | P9006950 A | | 4/1994 |
| HU | P0001425 A | | 3/2002 |
| NL | 8700306 | * | 9/1988 |

OTHER PUBLICATIONS

Patricia D. Mackenzie and C. Judson King "Combined Solvent Extraction and Stripping for Removal andisolation of Ammonia from Sour Waters" Ind. Eng. Chem. Process Des. Dev. 1985, 24, 1192-1200.*

The McNally Insitute "Controlling Temperature" Nov 17, 1999 "http://www.mcnallyinstitute.com/04-html/4-6.html".*

Answers.com "definition of mesophile" accessed Nov. 15, 2006.*

Brad C. Joern and Sarah L. Brichford "Calculating Manure and Manure Nutrient Application Rates" Agronomy Guide AY-277 Soils Purdue University Cooperative Extension Service Aug. 1993.*

Takashi Asano "Wastewater Reclamation and Reuse" CRC Press 1998.* abriel Bitton "Wastewater Microbiology" 2nd Ed Wiley 1999.*

Canh, T.T., et al. "Dietary Carbohydrates Alter the Fecal Composition and pH and the Ammonia Emission from Slurry of Growing Pigs", Journal of Animal Science. 1998, 76(7), pp. 1887-1895.*

Jungbluth, T. et al "Cofermentation of liquid manure and beets as a regenerative energy source" [online], [retrieved on Jun. 20, 2003]. Retrieved from the Internet <URL: http://www.uni-hohenheim.de/13ve/00217110/01492041.htm>, Mar. 12, 2002, 1 page.*

Jungbluth, T. et al "Nutrient Transport and Separation Behavior during luquid-solid separation of liquid manure" [online], [retrieved on Jun. 20, 2003]. Retrieved from the Internet <URL: http://www.uni-hohenheim.de/13ve/00217110/01488041.htm>, Mar. 12, 2002, 1 page.*

Baserga, U. and Egger, K. "Digestion of Energy Grass for Biogas Production" [online], [retrieved on Jun. 20, 2003]. Retrieved from the Internet <URL: http://www.biogas.ch/f+e/grasbasi.htm>, (Jul. 1999), 5 pages.*

Edelmann, W. et al "Two Step Anaerobic Digestion of Biogenic Solid Wastes" [online], [retrieved on Jun. 20, 2003]. Retrieved from the Internet <URL: http://www.biogas.ch/f+e/2stede.htm>, (Oct. 2000), 4 pages.*

Biogas Forum "Hygenic Considerations Concerning Co-digestion of MSW in Agricultural Biogas Plants" [online], [retrieved on Jun. 20, 2003]. Retrieved from the Internet <URL: http://www.biogas.ch.f+e/hygiene.htm>, (Jul. 1999), 2 pages.*

Engeli, H. et al "Membrane Treatment of Effluents from Anaerobic Digestion of Solid Waste" [online], [retrieved on Jan. 24, 2001]. Retrieved from the Internet <URL: www.biogas.ch/f+e/memen.htm>, (Oct. 2000), 5 pages.*

Center for Economic Studies, Energy, Transport and Environment (CEETA) "Anaerobic Digestion and Biogas" [online], [retrieved on Jan. 24, 2001]. Retrieved from the Internet <URL: http://riera.ceeeta.pt/images/ukbio__mass.htm>. 2001, 2 pages.*

Liao, P.H., et al, "Removal of Nitrogen from Swine Manure Wastewaters by Ammonia Stripping" Bioresour-technol. 1995, 54(1), pp. 17-20. [online], [retrieved 2004]. Retrieved from the Internet <URL: http://www.nal.usda.gov/wqic/Bibliographies/swine2.htm>, 1 page (abstract only).*

Fraunhofer IGB "Environmentally Friendly Reprocessing and Utilization of Liquid Manure" [online], [retrieved on Jan. 17, 2001]. Retrieved from the Internet <URL: http://igb.fhg.de/UWBio/en/Manure/en.html>, 1999, 2 pages.*

Rovel, Jean-Marie et al. Process for the Treatment of Urban or Industrial Residual Sludge by Aerobic Digestion, FR 2711980, May 12, 1999.

Fryklind, K. E., Anlæg til behandling af latringjødning og lign. Med ulæsket kalk, Norway, No. 17615, Jun. 20, 1997.

Cervenka, Jan et al., Method for Manufacturing Liquid Manure From Excrements From Utility Cattle, DE 3603 739, Aug. 7, 1986.

Kuehn, Horst et a., Manure treatment in two stages, to release ammonia and concentrate slurry, DE 4444032, May 2, 1996.

Langhans, Gerhard, Simultaneous treatment of organic waste prods., e.g. sewage—by subjecting streams of coarse prod. free waste to hydrolysing rotting, densifying and composing, DE 4201166, Jul. 22, 1993.

Munnecke, Gustav-Adolf, Process for extracting the ammonia from liquid manure and the conversion thereof into concentrated ammonia (NH3) water, DE 3737747, May 18, 1989.

Biogas production by co-fermentation of harvested crops and organic waste, DE 19828889, Dec. 23, 1999.

Hygienic, efficient, biogas-fired electrical power generation plant useful for cadavers, agricultural- and animal wastes, DE 19809299, Sep. 9, 1999.

Gerstner, Erwin et al., Preparation of solid, pelletised fertiliser using liquid manure, DE 19644613, Apr. 30, 1998.

Schroeder Ines, et al., Safe and useful disposal method for animal body parts, DE 19628521, Jan. 15, 1998.

Method of hygienization in connection with composting of large-scale kitchen refuse, DE 19625288, Jan. 9, 1997.

Processing of animal cadaver(s) to yield bio-gas and liq. fertilizer, DE 19623163, Dec. 5, 1996.

Bernstein, Fritz et al., Nitrogen recovery from liquid manure or agricultural effluent, DE 19615063, Sep. 11, 1997.

Chemical hydrolysis of proteinaceous broth, animal waste material and waste material from animal organs, EP 1021958, Jul. 26, 2000.

Dolle, Lothar, et al., Process for treating biowaste, EP 0866042, Sep. 23, 1998.

Drese, Jan Theo, A process and an apparatus for treatment of manure, in particular liquid manure, EP 0351922, Jan. 24, 1990.

Johansen, Kjeld, A method for anaerobic fermentation of organic substances, especially for the production of 'biogas' , EP 0286115, Apr. 8, 1998.

Lorre, Rudolf et al., Process for the preliminary treatment of organic slaughterhouse waste, EP 0218896, Apr. 22, 1987.

Calonje Velazquez Alfonso, Novel process for decontaminating waste (discharge) with a high organic-material content, ES 2100123, Jun. 1, 1997.

Broz Zdenek et al., Process for the treatment of liquid manure coming from the excrement of cattle bred for profit, FR 2576741, Aug. 8, 1986.

Newell, Patrick Joseph, Anaerobic treatment of waste to produce methane, GB 2013170, Aug. 8, 1979.

Oisu Gomu Kogyo, Method for Disposal of waste matter, JP 57012896, Jan. 22, 1982.

Norddahl, Birgir, Method and plant for the treatment of liquid organic waste, WO 9942423, Aug. 26, 1999.

Terlouw, Arie et al., Process and device for processing materials from which methane and other chemicals, being harmful to the environment, may escape, WO 9102582, Mar. 7, 1991.

Mathiesen, Niels, A method in the production of biogas, WO 8900548, Jan. 26, 1989.

Korsgard, Peter, Process and plant for producing biogas, WO 8400038, Jan. 5, 1984.

Chang et al., Lime pretreatment of switchgrass, Appl. Biochem. and Biotech., vol. 63-65, 1997, p. 3-19.

Cofermentation of liquid manure and beets as a regenerateve energy source, www.uni-hohenheim.de/i3ve/00217110/01492041.htm.

Nutrient transport and separation behavior during liquid-solid-separation of liquid manure, www.unihohenheim.de/i3ve/00217110/01488041.htm.

Baserga & Egger, Digestion of 'energy grass', www.biogas.ch/f+e/grasbasi.htm.

Edelman et al., Two step anaerobic digestion of biogenic solid wastes, www.biogas.ch/f+e/2stede.htm.

Hygienic consideration concerning co-digestion of MSW in agricultural biogas plants, www.biogas.ch/f+e/hygiene.htm.

Membrane treatment of effluents from anaerobic digestion of solid waste, www.biogas.ch/f+e/memen.htm.

Anaerobic digestion & biogas, Riera.ceeeta.pt/images/ukbio_mass.htm.

Liao et al., Removal of nitrogen from swine manure wastewaters by ammonia stripping, www.nal.usda.gov/wqic/Bibliographies/swine2.htm.

Environmentally friendly reprocessing and utilization of liquid manure, www.igb.fhg.de/Uwbio/en/Manure.en.html.

Johansen, P. S., Process for the utilisation of organic materials in energy production and production of reusable products, WO 02053878, Jul. 11, 2002.

Nishida, Shigeo, Method for treating organic wastewater/sludge of high nitrogen content, JP 2001113265, Oct. 20, 1999.

Nakazawa, Toshiaki, Treatment of ammonia nitrogen-contg. Waste water, JP 59039395, Aug. 27, 1982.

Otahara, Yoji, Treating method of organic waste matter, JP 53029278, Sep. 1, 1976.

McCrory, et al., "Additives to Reduce Ammonia and Odor Emissions from Livestock Wastes: A Review", *J. Environ. Qual.*, vol. 30, pp. 345-355, Mar.-Apr. 2001.

Azzam, et al., "Physicothermochemical Pretreatments of Food Processing Waste for Enhancing Anaerobic Digestion and Biogas Generation", *J. Environ. Sci. Health*, vol. A28(8), pp. 1629-1649, 1993.

Chang, et al., "Lime Pretreatment of Crop Residues Bagasse and Wheat Straw", *Applied Biochemistry and Biotechnology*, vol. 74, pp. 135-159, 1998.

Curreli, et al., "Mild alkaline/oxidative pretreatment of wheat straw", *Process Biochemistry*, vol. 32, No. 8, pp. 665-670, 1997.

Patel, et al., "Thermochemical Pretreatment of Water Hyacinth for Improved Biomethanation", *Applied Biochemistry and Biotechnology*, vol. 42, pp. 67-74, 1993.

Varhegyi, et al., "Kinetics of the thermal decomposition of cellulose in sealed vessels at elevated pressures. Effects of the presence of water on the reaction mechanism", *Journal of Analytical and Applied Pyrolysis*, vol. 26, pp. 159-174, 1993.

Argaman Y., Single sludge nitrogen removal in an oxidation ditch, Water Research, 18, pp. 1493-1500, 1984.

Banks C. J. and Humphreys P., The anaerobic treatment of a lignocellulosic substrate offering little natural pH buffering capacity, Water Science and Technology, 38, pp. 29-35, 1998.

Bendixen, H.J., Hygienic safety: results of scientific investigations in Denmark (sanitation requirements in Danis Biogas Plants), In Proceedings of the IEA workshop: "Hygienic and environmental aspects of anaerobic digestion: legislation and experiences in Europe." Universität Hohenheim, Stuttgart, Germany, pp. 27-47, 1999.

Benito G. G. and Cubero M. T. G., Ammonia elimination from beet sugar factory condensate streams by a stripping-reabsorbing system. Zuckerindustrie, 121, No. 9, pp. 721-726, 1996.

Bjerre A. B., Olesen A. B., Fernquist T., Ploger A., Schmidt A. S., Pre-treatment of wheat straw using combined wet oxidation and alkaline hydrolysis resulting in convertible cellulose and hemicelluloses, Biotechnology and Bioengineering, 49, pp. 568-577, 1996.

Blouin M., Bisaillon J. G., Beudet R., and Ishague M., Aerobic biodegradation of organic matter of swine waste, Biological Wastes, 25, pp. 127-139, 1988.

Bouhabila E. H., Aim R. B., and Buisson H., Micro filtration of activated sludge using submerged membrane with air bubbling (application to wastewater treatment). Desalination, 118, pp. 315-322, 1998.

Bunert U., Buczys R., Bruhns M., and Buchholz K., Ammonia stripping, Zuckerindustrie, 120, No. 11, pp. 960-969, 1995.

Burton C. H., Sneath R. W., Misselbrook T. H., and Pain B. F., Effect of farmscale aerobic treatment of piggery slurry on odour concentration, intensity and offensiveness, Journal of Agricultural Engineering Research, 71, 203-211, 1998.

Camarro L., Diaz J. M. and Romero F., Final treatments for anaerobically digested piggery effluents, Biomass and Bioenergy, 11, pp. 483-489, 1996.

Chacuk A., Zarzycki R., and Iciek J., A mathematical model of absorption stripping columns for removal of ammonia from condensates, Zuckerindustrie, 119, No. 12, pp. 1008-1015, 1994.

Cheung K. C., Chu L. M., and Wong M. H., Ammonia stripping as a pre-treatment for landfill leachate, Water Air and Soil Pollution, 94, pp. 209-221, 1997.

Chynoweth D. P., Owens J. M., and Legrand R., Renewable methane from anaerobic digestion of biomass, Renewable Energy, 22, pp. 1-8, 2001.

Colleran E., Wilkie A., Barry M., Faherty G., O'kelly N. and Reynolds P. J., One and two stage anaerobic filter digestion of agricultural wastes, Third Int. Symp. on Anaerobic Digestion, Boston MA, pp. 285-312, 1983.

Doyle Y. and de la Noüe J., Aerobic treatment of swine manure: Physico-chemical aspects, Biological Wastes, 22, pp. 187-208, 1987.

Dugba P. N., and Zhang R., Treatment of dairy wastewater with two-stage anaerobic sequencing batch reactor systems—thermopile versus mesopile operations, Bioresource Technology, 68, pp. 225-233, 1999.

Engelhardt N., Firk W., and Warnken W., Integration of membrane filtration into the activated sludge process in municipal wastewater treatment, Water Science and Technology, 38, pp. 429-436, 1998.

Eriksen L., Andreasen P. Ilsoe B., Inactivation of Ascaris suum eggs during storage in lime treated sewage sludge, Water Research, 30, pp. 1026-1029, 1996.

Ghosh S., Ombregt J. P., and Pipyn P., Methane production from industrial wastes by two-phase digestion, Water Research, 19, pp. 1083-1088, 1985.

Gönenc I. E. and Harremoës P., Nitrification in rotating disc systems-I. Criteria for transition from oxygen to ammonia rate limitation, Water Research, 19, pp. 1119-1127, 1985.

Gunaseelan V. N., Anaerobic digestion of biomass for methane production: A review, Biomass and Bioenergy, 13, pp. 83-114, 1997.

Gustavsson L., Borjesson P., Bengt J., Svenningsson P., Reducing $CO_2$ emissions by substituting biomass for fossil fuels, Energy, 20, pp. 1097-1113, 1995.

Han Y., Sung S., and Dague R. R., Temperature-phased anaerobic digestion of wastewater sludges, Water Science and Technology, 36, pp. 367-374, 1997.

Hansen K. H., Angelidaki I., Ahring B. K., Anaerobic digestion of swine manure: inhibition by ammonia, Water Research, 32, pp. 5-12, 1998.

Higgins M. J. and Novak J. T., The effects of cat ions on the settling and dewatering of activated sludge's Laboratory results, Water Environment Research, 69, pp. 215-224, 1997.

Jarvis Å., Nordberg Å., Jarlsvik T., Mathiesen B., and Svensson B. H., Improvement of a grass-clover silage-fed biogas process by the addition of cobalt, Biomass and Bioenergy, 12, pp. 453-460, 1997.

Jewell W. J., Cummings R. J., and Richards B. K., Methane fermentation of energy crops: maximum conversion kinetics and in situ biogas purification, Biomass and Bioenergy, 5, pp. 261-278, 1993.

Kayhanian M., Performance of high-solids anaerobic digestion process under various ammonia concentrations, Journal of Chemical Technology and Biotechnology, 59, pp. 349-352, 1994.

Krylova N. I., Khabiboulline R. E., Naumova R. P. Nagel M. A., The influence of ammonium and methods for removal during the anaerobic treatment of poultry manure, Journal of Chemical Technology and Biotechnology, 70, pp. 99-105, 1997.

Kuch P. J., Crosswhite W. M., The agricultural regulatory framework and biomass production, Biomass and Bioenergy, 14, pp. 333-339, 1998.

Li Y. Y., and Noike T., Upgrading of anaerobic digestion of waste activated sludge by thermal pre-treatment, Water Science and Technology, 26, pp. 3-4, 1992.

McCarty P. L., Young L. Y., Gossett J. M., Stuckey D. C., and Healy Jr. J. B., Heat treatment for increasing methane yield from organic materials, Microbial energy conversion, H.G. Schlegel and J. Barnea (ed.), Stanford University, California 94305, USA, pp. 179-199, 1977.

Møller H. B., Lund I., and Sommer S. G., Solid-liquid separation of livestock slurry: efficiency and cost, Bioresource Technology, 74, pp. 223-229, 1999.

Pagilla K. R., Kim H., and Cheunbarn T., Aerobic thermopile and anaerobic mesopile treatment of swine waste, Water Research, 34, pp. 2747-2753, 2000.

Sanin F. D., and Vesilind P. A., Synthetic sludge: a physical/chemical model in understanding bio flocculation, Water Environment Research, 68, pp. 927-933, 1996.

Schmidt A. S. and Thomsen A. B., Optimisation of wet oxidation pre-treatment of wheat straw, Bioresource Technology, 64, pp. 139-152, 1998.

Scott J. A.; Neilson D. J. Liu W., and Boon P. N., A dual function membrane bioreactor system for enhanced aerobic remediation of high-strength industrial waste, Water Science and Technology, 38, pp. 413-420, 1998.

Silva C. M., Reeve D. W., Husain H., Rabie H. R., and Woodhouse K. A., Model for flux prediction in high-shear microfiltration systems, Journal of Membrane Science, 173, pp. 87-98, 2000.

Sims R. H. E., Bioenergy—a renewable carbon sink, Renewable Energy, 22, pp. 31-37, 2001.

Sirohi S. K. and Rai S. N., Optimisation of treatment conditions of wheat straw with lime: Effect of concentration, moisture content and treatment time on chemical composition and in vitro digestibility, Animal Feed Science and Technology, 74, pp. 7-62, 1998.

Tanaka S., Kobayashi T. Kamiyama K. and Bildan M. L. N. S., Effects of thermo chemical pre-treatment on the anaerobic digestion of waste activated sludge, Water Science and Technology, 35, pp. 209-215, 1997.

Turner C. and Burton C. H., The inactivation of viruses in pig slurries: a review, Bioresource Technology, 61, pp. 9-20, 1997.

Vardar-Sukan F., Foaming: consequences, prevention and destruction, Biotechnology Advances, 16, pp. 913-948, 1998.

Visvanathan C., Yang B-S., Muttamara S., and Maythanukhraw R., Application of air back flushing in membrane bioreactor, Water Science and Technology, 36, pp. 259-266, 1997.

Wang Q., Noguchi C. K:, Kuninobu M., Hara Y., Kakimoto K. Ogawa H. I. and Kato Y., Influence of hydraulic retention time on anaerobic digestion of pre-treated sludge, Biotechnology Techniques, 11, pp. 105-108, 1997.

Wang Q., Noguchi C., Hara Y., Sharon C., Kakimoto K., and Kato Y., Studies on anaerobic digestion mechanisms: Influence of pre-treatment temperature on biodegradation of waste activated sludge, Environmental Technology, 18, pp. 999-1008, 1997.

Wyman C. E. and Goodman B. J., Biotechnology for production of fuels chemicals and materials from biomass, Applied Biochemistry and Biotechnology, 39, pp. 41-59, 1993.

Zaloum R., Coron-Ramstrim A.-F. Gehr R., Final clarification by integrated filtration within the activated sludge aeration tank, Environmental Technology, 17, pp. 1007-1014, 1996.

Garraway, J.L., "Investigations on the Aerobic Treatment of Pig Slurry", *Agricultural Wastes*, vol. 4, pp. 131-142, 1982.

Ginnivan, M.J., "The Effect of Aeration Rates on Odour and Solids of Pig Slurry", *Agricultural Wastes*, vol. 7, pp. 197-207, 1983.

* cited by examiner

CONCEPT FOR SLURRY SEPARATION AND BIOGAS PRODUCTION

TECHNICAL FIELD OF THE INVENTION

In a first aspect, the present invention concerns an anaerobic digestion of animal manures, energy crops and similar organic substrates. The process is capable of refining nutrients comprised in the digested biomass to fertilizers of commercial quality. The biogas and slurry separation system according to the present invention is preferably integrated with the operations of animal husbandries into a total concept in which the internal and external performances of animal husbandries are optimised.

One additional aspect of the invention is the possible application for disposing off animal waste in the form of animal carcasses, slaughterhouse waste, meat and bone meal, etc. The waste is refined in the plant to fertilizers to be applied to agricultural land. A possible content of BSE-prions or other prions is substantially reduced if not eliminated in the whole process. The animal produce is in this concept not used as fodder but fertilizer. The destruction of possible BSE prions in the biomass treated in the plant in combination with the use of the refined biomass as fertilizer in stead of fodder substantially reduces if not eliminates the risk of infecting animals or humans with BSE-prions or modifications thereof.

The internal performances concern quality aspects related to the management of the animal houses and include industrial hygiene, animal welfare, control of gaseous and dust emissions and food safety. The external performances concern mainly energy production and control of emissions to the environment of nutrients and greenhouse gasses and the sale of high quality food products as well as an alternative way for disposing of animal carcasses and the like.

BACKGROUND OF THE INVENTION

Ammonia Stripping

The chemistry of ammonia is well known and stripping of ammonia from different fluids is a well known industrial process. It has for example been employed by the sugar industry (Bunert et al. 1995; Chacuk et al. 1994; Benito and Cubero 1996) and by municipalities as treatment of landfill reject (Cheung et al. 1997). Ammonia may also be stripped from pig slurry based on the same principles as in the industry (Liao et al. 1995).

The basic principle for large scale stripping of ammonia is increasing pH and aerating and heating of the wastewater or the slurry. It is often $Ca(OH)_2$ or $CaO$ which is used to increase pH. Other bases may be employed such as NaOH or KOH. The lime, however, is used on an industrial scale by for instance the cement industry and is therefore cheap and readily available as bulk ware.

Where the stripped ammonia is absorbed and an ammonia concentrate is produced sulphuric acid is often used in the absorption column. Sulphuric acid is an industrial bulk ware and is available in a technical quality appropriate for use in absorption columns stripping ammonia from slurry and other waste waters (e.g. Sacuk et al. 1994).

Based on the experience gained in the sugar industry it has been found that the most appropriate parameter values are: Temperature 70° C.; a pH in the range of about 10-12; and a liquid gas ration of 1:800, 96% affectivity.

For stripping of ammonia from slurry it is found that the optimal parameter values at low temperature are: temperature 22° C.; pH of about 10-12; liquid gas ratio of 1:2000, 90% affectivity, 150 h operation (Liao et al. 1995).

REFERENCES

Benito G. G. and Cubero M. T. G. (1996) Ammonia elimination from beet sugar factory condensate streams by a stripping-reabsorbing system. Zuckerindustrie 121, 721-726.

Bunert U., Buczys R., Bruhns M., and Buchholz K. (1995) Ammonia stripping. Zuckerindustrie 120, 960-969.

Chacuk A., Zarzycki R., and Iciek J. (1994) A mathematical model of absorption stripping columns for removal of ammonia from condensates. Zuckerindustrie 119, 1008-1015.

Cheung K. C., Chu L. M., and Wong M. H. (1997) Ammonia stripping as a pretreatment for landfill leachate. Water Air and Soil Pollution 94, 209-221.

Liao, P. H., Chen A., and Lo K. V. (1995) Removal of nitrogen from swine manure wastewaters by ammonia stripping. Biotechnology & Applied Microbiology 54, 1720.

Alkali and Thermal Hydrolyses

Thermal pre-treatment of biomass before anaerobic digestion is a technology which is well described in the literature, e.g. Li and Noike (1992). In resent years thermal pre-treatment of municipal waste has also been used on a commercial scale by Cambi A S, Billingstad, Norway.

Wang et al. (1997a and b) found that thermal pre-treatment of municipal waste at 60° C. and a hydraulic residence time of 8 days resulted in an increased methane production of 52.1%. A similar result was found by Tanaka et al. (1997), the combination however with alkali hydrolyses gave the highest increase in gas yield (200%). McCarty et al. have performed a series of studies showing that the combination of thermal and alkali hydrolysis increases the gas yield substantially. The pH however, shall be about 10 to 12, and preferably 11 or higher, before the chemical hydrolysis shall produce a significant additional gas yield.

The results of Wang et al. (1997) shows that the default parameter values for ammonia stripping under section 2.1 (the pH of about 10 to 12, preferably 11 or more, and the temperature of about 70° C. or more during a week) will increase the gas yield.

REFERENCES

Li Y. Y., and Noike T. (1992) Upgrading of anaerobic digestion of waste activated sludge by thermal pre-treatment. Water Science and Technology 26, 3-4.

McCarty P. L., Young L. Y., Gossett J. M., Stuckey D. C., and Healy Jr. J. B. Heat treatment for increasing methane yield from organic materials. Stanford University, California 94305, USA.

Tanaka S., Kobayashi T. Kamiyama K. and Bildan M. L. N. S. (1997) Effects of thermo chemical pre-treatment on the anaerobic digestion of waste activated sludge. Water Science and Technology 35, 209-215.

Wang Q., Noguchi C., Hara Y., Sharon C., Kakimoto K., and Kato Y. (1997a) Studies on anaerobic digestion mechanisms: Influence of pre-treatment temperature on biodegradation of waste activated sludge. Environmental Technology 18, 999-1008.

Wang Q., Noguchi C. K., Kuninobu M., Hara Y., Kakimoto K. Ogawa H. I. And Kato Y. (1997b) Influence of hydraulic retention time on anaerobic digestion of pre-treated sludge. Biotechnology Techniques 11, 105-108.

Sanitation

Sanitation of slurry before transporting and field application constitute an important strategy for reducing the risk of spreading zoo noses and veterinary vira, bacteria and parasites (e.g. Bendixen 1999). Anaerobe digestion has proven effective in reducing the number of zoo noses in slurries but it does not eliminate these organisms (Bendixen 1999; Pagilla et al. 2000). The use of CaO for sanitation of sewage sludge has also shown that Ascaris eggs and parasites (Eriksen et al. 1996) and virus are reduced substantially but not completely (Turner and Burton 1997).

REFERENCES

Bendixen H. J. Hygienic safety—results of scientific investigations in Denmark (sanitation requirements in Danish biogas plants). Hohenheimer Seminar IEA Bioenergy Workshop March 1999.

Eriksen L., Andreasen P. Ilsoe B. (1996) Inactivation of Ascaris suum eggs during storage in lime treated sewage sludge. Water Research 30, 1026-1029.

Pagilla K. R., Kim H., and Cheunbarn T. (2000) Aerobic thermopile and anaerobic mesopile treatment of swine waste. Water Research 34, 2747-2753.

Turner C. and Burton C. H. (1997) The inactivation of viruses in pig slurries: a review. Bioresource Technology 61, 9-20.

Foam

Foam formation associated with anaerobic digestion may constitute a serious problem for operating the fermentors. A number of substances for remediation of foam are commercially available including different polymers, plant oils (e.g. rape oil) and different salts (e.g. Vardar-Sukan 1998). However, polymers may cause environmental concerns and are often expensive and ineffective.

REFERENCES

Vardar-Sukan F. (1998) Foaming: consequences, prevention and destruction. Biotechnology Advances 16, 913-948.

Flocculation

Calcium-ions are a well known as means to flocculate substances and particles due to the formation of calcium-bridges between organic and inorganic substances in solution or suspension thus forming "flocks" of particles (e.g. Sanin and Vesilind 1996). For this reason calcium has been used for dewatering of sewage sludge (Higgins and Novak 1997).

REFERENCES

Higgins M. J. and Novak J. T. (1997). The effects of cat ions on the settling and de-watering of activated sludge's: Laboratory results. Water Environment Research 69, 215-224.

Sanin F. D., and Vesilind P. A. (1996) Synthetic sludge: A physical/chemical model in understanding bio flocculation. Water Environment Research 68, 927-933.

Decanter Centrifuge Slurry Separation, P Stripping

Decanter centrifuges have been applied to a number of industrial processes during the last 100 years.

Among recent examples of the use of decanter centrifuges is the Novo Nordisk plant in Kalundborg where all waste from the large insulin fermentation units is treated. Also municipal sludge is dewatered by means of decanter centrifuges (Alfa Laval A/S). The decanter centrifuges separate the dry (solid) matter from the sludge or wastes, while the water phase or the reject water is lead to a conventional sewage treatment plant.

Experiments with separation of cattle, pig and degassed slurry show firstly that decanter centrifuges can treat all manures without any difficulties. It has also been found that the centrifuges remove approximately 70% dry matter, 60-80% total P and only 14% of total N from a slurry previously digested thermopile (Møller et al. 1999; Møller 2000a). The corresponding values for raw slurry from cattle and pigs were somewhat lower. It should be noted that only 14% of total N is removed from the waste.

The total treatment cost has been calculated to 5 Dkr. per $m^3$ slurry at a slurry volume of 20.000 tons or more. In those situations where the slurry volume exceeds 20.000 tons the decanter centrifuges are cost efficient and cheap instruments for separation of dry matter and total P from slurry (Møoller et al. 1999).

Under normal circumstances it is without any interest to treat slurry in a decanter centrifuge, because it is not associated with any volume reduction or other advantages to the farmers. The ammonia loss following field application of treated slurry may be somewhat reduced due to an increased infiltration rate into the soil (Møller 2000b), but this is by far sufficient incentive to farmers for use of decanter centrifuges.

REFERENCES

Møller H. B. (2000a) Opkoncentrering af næringsstoffer i husdyrgødning med dekantercentrifuge og skruepresse. Notat 12. September 2000, Forskningscenter Bygholm.

Møller H. B. (2000b) Gode resultater med at separere gylle. Maskinbladet 25. august 2000.

Møller H. B., Lund I., and Sommer S. G. (1999) Solid-liquid separation of livestock slurry: efficiency and cost.

Alfa Laval A/S Gylleseparering. Separeringsresultater med decantercentrifuge.

P-Precipitation

Dissolved P is precipitated almost immediately following addition of Ca as calcium phosphate $Ca_3(PO_4)_2$ (Cheung et al. 1995).

REFERENCES

Cheung K. C., Chu L. M., and Wong M. H. (1997) Ammonia stripping as a pretreatment for landfill leachate. Water Air and Soil Pollution 94, 209-221.

Prevention of Struvite Formation

It is an additional important aspect that the P precipitation in combination with the stripping of ammonia prevents the formation of struvite ($MgNH_4PO_4$). Struvite constitutes a significant working problem in heat-exchangers, transport in pipes, etc. (Krüger 1993). The mechanism is P-removal through formation of $CaPO_4$ as well as removal of ammonia through the stripping process. The P and ammonia removal prevents formation of struvite.

Krüger (1993) Struvit dannelse i biogasfeellesanlæg. Krüger WasteSystems AS.

Reject Water Filtration

Systems for final treatment and membrane filtration of reject water have been presented over the past 10 years in the form of e.g. membrane plants (BioScan A/S, Ansager ApS) and plants based on steam compression (Funki A/S, Bjørnkjær Maskinfabrikker A/S). These systems generally result in a gross cost per $m^3$ slurry of 50-100 Dkr. The plants are further not able to treat other types of manure but pig slurry.

The reduction of volume obtained by these plants is often not more than 50-60%, meaning that field application of the remains in any case depends on conventional devices. Hence, these plants are not competitive due to the cost level and/or a limited volume reduction.

However, it is important to consider and recognise the cost level of these plants. It is also valuable to consider the energy use in the form electricity which the mechanical steam compression gives rise to, i.e. about 50 kWh per tons treated slurry. This means that membranes, under the assumption that the water phase to be filtered consists of salts and minimal amounts of dry matter only, which do not produce scaling or fouling problems, may be able to out compete evaporation technologies.

REFERENCES

Argaman Y. (1984) Single sludge nitrogen removal in an oxidation ditch. Water Research 18, 1493-1500.

Blouin M., Bisaillon J. G., Beudet R., and Ishague M. (1988) Aerobic biodegradation of organic matter of swine waste. Biological Wastes 25, 127-139.

Bouhabila E. H., Aim R. B., and Buisson H. (1998) Micro filtration of activated sludge using submerged membrane with air bubbling (application to wastewater treatment). Desalination 118, 315-322.

Burton C. H., Sneath R. W., Misselbrook T. H., and Pain B. F. (1998) Journal of Agricultural Engineering Research 71, 203.

Camarro L., Diaz J. M. and Romero F. (1996) Final treatments for anaerobically digested piggery effluents. Biomass and Bioenergy 11, 483-489.

Doyle Y. and de la Noüe J. (1987) Aerobic treatment of swine manure: Physicochemical aspects. Biological Wastes 22, 187-208.

Engelhardt N., Firk W., and Wamken W (1998) Integration of membrane filtration into the activated sludge process in municipal wastewater treatment. Water Science and Technology 38, 429-436.

Garraway J. L. (1982) Investigations on the aerobic treatment of pig slurry. Agricultural Wastes 4,131-142.

Ginnivan M. J. (1983) The effect of aeration on odour and solids of pig slurries. Agricultural Wastes 7,197-207.

Gönenc I. E. and Harremoës P. (1985) Nitrification in rotating disc systems-I. Criteria for transition from oxygen to ammonia rate limitation. Water Research 19, 1119-1127.

Scott J. A.; Neilson D. J. Liu W., and Boon P. N. (1998) A dual function membrane bioreactor system for enhanced aerobic remediation of high-strength industrial waste. Water Science and Technology 38, 413-420.

Silva C. M., Reeve D. W., Husain H., Rabie H. R., and Woodhouse K. A. (2000) Journal of Membrane Science 173, 87-98.

Visvanathan C., Yang B-S., Muttamara S., and Maythanukhraw R. (1997) Application of air back flushing in membrane bioreactor. Water Science and Technology 36, 259-266.

Zaloum R., Coron-Ramstrim A.-F. Gehr R. (1996) Final clarification by integrated filtration within the activated sludge aeration tank. Environmental Technology 17, 1007-1014.

Lime Cooking

A thermal and chemical hydrolysis at temperatures less than 100° C. and therefore pressures at about 1 atm represents one option for increasing the availability of the organic matter for biogas generation. However, the complex carbohydrates such as cellulose, hemicelluloses and lignin is not completely hydrolysed by such treatments. Fibres from straw, maize and other crops are not made available for methane formation by such treatments (Bjerre et al 1996; Schmidt and Thomsen 1998; Thomsen and Schmidt 1999; Sirohi and Rai 1998). An alkali lime cooking at moderate temperatures above 100° C. is well suited to render these substrates available to microbial decomposition (Curelli et al. 1997; Chang et al. 1997; Chang et al. 1998).

This treatment, when applied to cellulose fibres from sugar cane cut to 0.5 mm (with 4% CaO, 200° C. and 16 bar), disintegrates the cellulose to small organic acids as formic acid, acetic acid, lactic acid etc. The methane generation from treated cellulose is thus as high as 70% of the corresponding amount of carbohydrates as pure glucose (Azzam and Naser 1993). Also, green crops can be treated in a lime cooker, but at lower temperatures. It has been shown that the optimal result was achieved when water hyacinths were exposed to pH 11 and 121° C. (Patel et al. 1993).

Formation of PAH and of substances inhibitory to methane bacteria may be formed at elevated temperatures (Varhegyi et al. 1993; Patel et al. 1993). However, this phenomena has not been seen at the relatively moderate temperatures used in lime cooking as compared the pyrolysis (Azzam et al. 1993). During pyrolysis the temperatures are so high that the biomass disintegrates directly to gasses as hydrogen, methane and carbon monoxide but unfortunately also to PAH and other pollutants.

REFERENCES

Azzam A. M. and Nasr M. I. (1993) Physicothermochemical pre-treatments of food processing waste for enhancing anaerobic digestion and biogas fermentation. Journal of Environmental Science and Engineering 28, 1629-1649.

Bjerre A. B., Olesen A. B., Fernquist T., Ploger A., Schmidt A. S. (1996) Pretreatment of wheat straw using combined wet oxidation and alkaline hydrolysis resulting in convertible cellulose and hemicelluloses. Biotechnology and Bioengineering 49, 568-577.

Chang V. S., Nagwani M., Holtzapple M. T. (1998) Original articles—Lime pretreatment of crop residues bagasse and wheat straw. Applied Biochemistry and Biotechnology Part A—Enzyme Engineering and Biotechnology 74, 135-160.

Chang V. S., Barry B., Holtzapple M. T. (1997) Lime pretreatment of switchgrass. Applied Biochemistry and Biotechnology Part A—Enzyme Engineering and Biotechnology 63-65, 3-20.

Curelli N., Fadda M. B., Rescigno A., Rinaldi A. C., soddu G., Sollai E., Vaccargiu S.; Sanjust E., Rinaldi A. (1997) Mild alkaline/oxidative pretreatment of wheat straw. Process Biochemistry 32, 665-670.

Patel V., Desai M., and Madamwar D. (1993) Thermo chemical pre-treatment of water hyacinth for improved biomethanation. Applied Biochemistry and Biotechnology 42, 67-74.

Schmidt A. S. and Thomsen A. B. (1998) Optimisation of wet oxidation pretreatment of wheat straw. Bioresource Technology 64, 139-152.

Sirohi S. K. and Rai S. N. (1998) Optimisation of treatment conditions of wheat straw with lime: Effect of concentration, moisture content and treatment time on chemical composition and in vitro digestibility. Animal Feed Science and Technology 74, 57-62.

Thomsen A. B. and Schmidt A. S. (1999) Further development of chemical and biological processes for production of bio ethanol: optimisation of pre-treatment processes and characterisation of products. Rise National Laboratory, Roskilde, Denmark.

Varhegyi G., Szabo P., Mok W. S. L., and Antal M. J. (1993) Kinetics of the thermal decomposition of cellulose in sealed vessels at elevated pressures. Journal of Analytical and Applied Pyrolysis 26, 159-174.

Energy Crop Silage

The conventional use of energy crops is mainly in the form of solid fuel for burning (willow as wood chops, straw or whole seed) or as fuel for engines (rape oil). On an experimental basis beets and straw is used for production of ethanol (Parsby; Sims 2001; Gustavsson et al. 1995; Wyman and Goodman 1993; Kuch 1998). In other parts of the world the use of energy crops is widespread and subject to much research. The use of terrestrial as well as marine and freshwater plants is well documented (Gunaseelan 1997; Jewell et al. 1993; Jarwis et al 1997). Some studies would appear to indicate that anaerobic fermentation of energy crops is competitive to other uses of biomass (Chynoweth D. P., Owens J. M., and Legrand R. 2001).

The use of energy crops is well motivated. The use of straw is organised in a way which probably makes this practise a concept to be seen for a number of years to come. The use of wood chops seems to be economical and practical viable. Incineration of grain cereals on the other hand has given rise to ethical objections. The production of grain cereals is also inevitable associated with the use of fertilizers and pesticides and N-losses from the fields. N is also lost during the burning of the biomass.

REFERENCES

Beck J. Co-fermentation of liquid manure and beets as a regenerative energy. University of Hohenheim, Dep. Agricultural Engineering and Animal Production. Personal communication.

Chynoweth D. P., Owens J. M., and Legrand R. (2001) Renewable methane from anaerobic digestion of biomass. Renewable Energy 22, 1-8.

Gunaseelan V. N. (1997) Anaerobic digestion of biomass for methane production: A review. Biomass and Bioenergy 13, 83-114.

Gustavsson L, Borjesson P., Bengt J., Svenningsson P. (1995) Reducing $CO_2$ emissions by substituting biomass for fossil fuels. Energy 20, 1097-1113.

Jewell W. J., Cummings R. J., and Richards B. K. (1993) Methane fermentation of energy crops: maximum conversion kinetics and in situ biogas purification. Biomass and Bioenergy 5, 261-278.

Jarvis Å., Nordberg Å., Jarlsvik T., Mathiesen B., and Svensson B. H. (1997) Improvement of a grass-clover silage-fed biogas process by the addition of cobalt. Biomass and Bioenergy 12, 453-460.

Kuch P. J., Crosswhite W. M. (1998) The agricultural regulatory framework and biomass production. Biomass and Bioenergy 14, 333-339.

Parsby M. Halm og energiafgrøder—analyser af økonomi, energi og miljø. Rapport Nr. 87, Statens Jordbrugs og Fiskeriøkonomiske Institut.

Sims R. H. E. (2001) Bioenergy—a renewable carbon sink. Renewable Energy 22, 31-37.

Wyman C. E. and Goodman B. J. (1993) Biotechnology for production of fuels chemicals and materials from biomass. Applied Biochemistry and Biotechnology 39, 41-59.

Banks C. J. and Humphreys P. N. (1998) The anaerobic treatment of a lignocellulosic substrate offering little natural pH buffering capacity. Water Science and Technology 38, 29-35;

Colleran E., Wilkie A., Barry M., Faherty G., O'kelly N. and Reynolds P. J. (1983) One and two stage anaerobic filter digestion of agricultural wastes. Third Int Symp. on Anaerobic Digestion, pp. 285-312, Boston Mass. (1983).

Dugba P. N., and Zhang R. (1999) Treatment of dairy wastewater with two-stage anaerobic sequencing batch reactor systems—thermopile versus mesopile operatons. Bioresource Technology 68, 225-233.

Ghosh S., Ombregt J. P., and Pipyn P. (1985) Methane production from industrial wastes by two-phase digestion. Water Research 19, 1083-1088.

Han Y., Sung S., and Dague R. R. (1997) Temperature-phased anaerobic digestion of wastewater sludge's. Water Science and Technology 36, 367-374.

Krylova N. I., Khabiboulline R. E., Naumova R. P. Nagel M. A. (1997) The influence of ammonium and methods for removal during the anaerobic treatment of poultry manure. Journal of Chemical Technology and Biotechnology 70, 99-105.

Hansen K. H., Angelidaki I., Ahring B. K. (1998) Anaerobic digestion of swine manure: inhibition by ammonia. Water Research 32, 5-12.

Kayhanian M. (1994) Performance of high-solids anaerobic digestion process under various ammonia concentrations. Journal of Chemical Technology and Biotechnology 59, 349-352.

Wang Q., Noguchi C. K., Kuninobu M., Hara Y., Kakimoto K., Ogawa H. I., and Kato Y. (1997) Influence of hydraulic retention time on anaerobic digestion of pre-treated sludge. Biotechnology Techniques 11, 105-108.

Disposal Systems for Animal Cadavers etc.

The present disposal system for animal cadavers is organised by registering plants which are licensed to process the animal cadavers. The cadavers are primarily used for production of meat and bone meal which traditionally have been used for animal foodstuff.

The present BSE-crisis have stopped this practise by a regulatory order from the EU-commission, stating that meat and bone meal cannot be used as animal foodstuff.

The livestock sector and associated businesses in Europe thus face the challenge to find alternative use of meat and bone meal or alternative ways of disposing off the meal. However, this is a difficult task because of the constraints imposed by the risk of spreading BSE prions or other prions possibly present in the meal or other fractions of animal cadavers.

The use of meat and bone meal or animal cadavers in conventional biogas plants is certainly not advisable and only partly possible. The processing of animal cadavers in plants licensed to process such animals is usually performed at temperatures around 130° C., with pressure around 2-3 bar with a retention time of 20 min. Such conditions are not to be found in conventional biogas plants.

The below mentioned patents and patent applications form part of the prior art.

DE3737747 describes a plant and a process to stripping of N. CaO is added to the manure by which the ammonia is stripped, said ammonia is absorbed in a water solution containing hydrochloric acid. A number of aspects of the invention are not described by this reference. This applies, among other things, to the pre-treatment such as the alkaline hydrolysis, welfare in the animal houses, utilization of energy crops, absorbing of ammonia in a sulfur solution, the precipitation of P, prevention of struvite formation etc. and the use of biogas through a local gas engine or through an established pipeline for natural gas.

DE4201166 describes a method of concurrent treatment of different organic waste products, in which the waste products are separated into three fractions containing different amounts of solid components. Solid fractions are homogenised before fermentation and biogas production. A number of aspects of the invention are not described by this reference. This applies, among other things, to the pre-treatment such as the alkaline hydrolysis, welfare in the animal houses, utilization of energy crops, absorbing of ammonia in a sulfur solution, the precipitation of P, prevention of struvite formation etc. and the use of biogas through a local gas engine or through an established pipeline for natural gas.

DE4444032 describes a plant and a process in which slurry i the first reactor is stirred, aerated and added lime to pH 9.5 to strip ammonia. In the second reactor a salt containing ferro and a polymer are added to neutralise the slurry and precipitate solids. A number of aspects of the invention are not described by this reference. This applies, among other things, to the pre-treatment such as the alkaline hydrolysis, welfare in the animal houses, utilization of energy crops, absorbing of ammonia in a sulfur solution, the precipitation of P, prevention of struvite formation etc. and the use of biogas through a local gas engine or through an established pipeline for natural gas.

DE196615063 describes a process in which ammonia is stripped from fermented manure. A number of aspects of the invention are not described by this reference. This applies, among other things, to the pre-treatment such as the alkaline hydrolysis, utilization of energi crops, the precipitation of P, prevention of struvite formation etc. and the use of biogas through a local gas engine or through an established pipeline for natural gas.

EP0286115 describes a method to production of biogas in which manure is added fat acids or compositions containing fat acids. A number of aspects of the invention are not described by this reference. This applies, among other things, to the pretreatment such as the alkaline hydrolysis, utilization of energi crops, the precipitation of P, prevention of struvite formation etc. and the use of biogas through a local gas engine or through an established pipeline for natural gas.

EP0351922 describes a plant and a process in which the stripping of ammonia, carbon dioxide and phosphate occurs from liquid manure. The manure is transported from the farm by tank cars to the plant where the slurry is treated with hot air and by that partly stripped of ammonia and carbon dioxide. The remaining part of the slurry is heated and lime is added to pH 10-11, by which more ammonia is stripped and calcium phosphate is formed. The stripped ammonia is absorbed in an acidic solution by the formation of ammonium salt, which is dried and utilized as fertilizers. A decanter centrifuge is used to separate solid parts from the slurry. A number of aspects of the invention are not described by this reference. This applies, among other things, to the pre-treatment such as the alkaline hydrolysis, welfare in the animal houses, utilization of energi crops, prevention of struvite formation etc. and the use of biogas through a local gas engine or through an established pipeline for natural gas.

ES2100123 describes a plant and a process in which liquid manure is cleaned. Organic components is degraded and precipitated solids is removed by decanter centrifugation. The liquid is added acid and is spread in the land or is further cleaned by aeration and by that stripping of ammonia. The cleaned liquid is diverted to a water purifying plant. A number of aspects of the invention are not described by this reference. This applies, among other things, to the pre-treatment such as the alkaline hydrolysis, welfare in the animal houses, stripping of ammonia at an early step, utilization of energi crops, prevention of struvite formation etc. and the use of biogas through a local gas engine or through an established pipeline for natural gas.

FR2576741 describes a process to the production of biogas by fermenting of liquid manure. The slurry is treated with lime and precipitated components is removed. A number of aspects of the invention are not described by this reference. This applies, among other things, to the pretreatment such as the alkaline hydrolysis, utilization of energi crops, the precipitation of P, prevention of struvite formation etc. and the use of biogas through a local gas engine or through an established pipeline for natural gas.

GB 2013170 describes a plant and a method to production of biogas. In the first reactor the organic material is acidified and the solid fraction is removed. The liquid fraction is diverted to the second reactor in which an anaerobic degradation occurs with the production of methane gas. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

DE19644613 describes a method to produce solid fertilisers from manure. The liquid manure is added substrate from the biogas production together with CaO or $Ca(OH)_2$. The stripped ammonia is collected. A number of aspects of the invention are not described by this reference. This applies, among other things, to the pretreatment such as the alkaline hydrolysis, utilization of energi crops, the precipitation of P, prevention of struvite formation etc. and the use of biogas through a local gas engine or through an established pipeline for natural gas.

DE19828889 describes co-fermentation of harvested crops and organic waste with the production of biogas. The material is homogenised and fermented. A number of aspects of the invention are not described by this reference. This applies, among other things, to the pre-treatment such as the alkaline hydrolysis, utilization of energi crops, the precipitation of P, prevention of struvite formation etc. and the use of biogas through a local gas engine or through an established pipeline for natural gas.

U.S. Pat. No. 4,041,182 describes a method to production of animal foodstuff from organic waste. A number of aspects of the invention are not described by this reference. This applies, among other things, to the pre-treatment such as the alkaline hydrolysis, utilization of energi crops, the precipitation of P, prevention of struvite formation etc. and the use of biogas through a local gas engine or through an established pipeline for natural gas.

U.S. Pat. No. 4,100,023 describes a plant and a process to the production of methane gas and fertilisers. In the first reactor an aerob degradation of the homogenised material is performed. In the second reactor which is heated, an anaerob degradation and the biogas production occurs. Fertilisers are produced as liquids. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 4,329,428 describes a plant for anaerobic decomposition, in particular material from various green plants, and the use of the produced biogas. The plant is based on the decomposition and caused by mesofilic or thermopile anaerobic bacteria. A number of aspects of the invention are not described by this reference. This applies, among other things, to the pre-treatment such as the alkaline hydrolysis, the stripping of ammonia, the precipitation of P, prevention of struvite formation etc. and the use of biogas through a local gas engine or through an established pipeline for natural gas.

U.S. Pat. No. 4,579,654 describes a plant and a process to produce biogas from organic materials. Solid materials are hydrolysed, acidified and fermented. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 4,668,250 describes a process in which ammonia is removed from the liquid fraction by aeration. A number of aspects of the invention are not described by this reference. This applies, among other things, to the pre-treatment such as the alkaline hydrolysis, utilization of energi crops, the precipitation of P, prevention of struvite formation etc. and the use of biogas through a local gas engine or through an established pipeline for natural gas.

U.S. Pat. No. 4,750,454 describes a plant for anaerobic digestion of animal manure and the use of the biogas produced by the process. The plant is based on decomposition caused by mesofilic or thermopile anaerobic bacteria and utilizes a local gas powdered engine equipped with a generator. A number of aspects of the invention are not described by this reference. This applies, among other things, to the pre-treatment such as the alkaline hydrolysis, the stripping of ammonia, the precipitation of P, prevention of struvite formation etc. and the use of biogas through a local gas engine or through an established pipeline for natural gas.

U.S. Pat. No. 5,071,559 describes a method to treatment of manure. The manure is added water and the mixture is acidified. Liquid is removed by steamproduction, which again is condensated in another reactor and treated anaerobic to produce biogas. The fermented liquid is fraction is then treated by an aerob process. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 5,296,147 describes a process to treat manure and other organic components. The organic waste fermentes and is then nitrified and further denitrified. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 5,389,258 describes a method to production of biogas from semi-solid and solid organic waste. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 5,494,587 describes a process with a catalytic treatment of manure including reduction of the nitrogen concentration. A number of aspects of the invention are not described by this reference. This applies, among other things, to the pre-treatment such as the alkaline hydrolysis, welfare in the animal houses, stripping of ammonia, utilization of energi crops, prevention of struvite formation etc. and the use of biogas through a local gas engine or through an established pipeline for natural gas.

U.S. Pat. No. 5,525,229 describes a general procedure for anaerobic digestion of organic substrates under thermopile as well as mesofilic conditions.

U.S. Pat. No. 5,593,590 describes separation and treatment of liquid and solid organic waste following a separation of the two fractions. The liquid fraction is fermented with the production of biogas followed by removing of precipitated solid components, which partly is recirculated in the process. The solid fraction is treated in an aerob process and is produced into compost, fertilisers or animal foodstuff. Part of the produced biogas comprising methane and $CO_2$ is reuse to the reduction of the pH level in the liquid fraction by a CO2 absorption. Solids is precipitated from liquid fractions e.g. by a decanter centrifuge, and ammonia is stripped from the liquid by a pH of 9-10. Reject water can be used to clean stables. A number of aspects of the invention are not described by this reference. This applies, among other things, to the pretreatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,616,163 describes a method to treatment of manure by which nitrogen is utilised in the production of fertilisers. Liquid manure is added CO2 and/or CaSO4 by which ammonia is stripped. A number of aspects of the invention are not described by this reference. This applies, among other things, to the pre-treatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,656,059 describes a method to treat manure by which nitrogen is utilised in the production of fertilisers more or less by nitrification. A number of aspects of the invention are not described by this reference. This applies, among other things, to the pre-treatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,670,047 describes a general procedure for anaerobic decomposition of organic substrates to gases.

U.S. Pat. No. 5,681,481 U.S. Pat. No. 5,783,073 and U.S. Pat. No. 5,851,404 describes a process and an apparatus to stabilising of slurry. Lime is added to pH≧12 and the mass is heated to at least 50.degree.C for 12 hours. Ammonia is stripped, and is either discharged into the atmosphere or recirculated in the system. A 'preheat chamber' can be used as well as decanter centrifugation as well as mixing of the sludge to keep it in a liquid condition. The sludge is spread to land. A number of aspects of the invention are not described by this reference. This applies, among other things, to the pre-treatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,746,919 describes a process in which organic waste is treated in a thermofil anaerob reactor followed by treatment in a mesofil anaerob reactor. In both reactors a production of methane gas occurs. A number of aspects of the invention are not described by this reference. This applies, among other things, to the pre-treatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,773,526 describes a process in which liquid and solid organic waste is fermented first by a mesofil process and thereby by a thermofil process. Solid components is hydrolysed and acidifies. A number of aspects of the invention are not described by this reference. This applies, among other things, to the pre-treatment such as the alkaline hydrolysis, welfare in the animal houses by use of straw, stripping of ammonia before biogas production, utilization of energi crops, prevention of struvite formation etc. and the use of biogas through a local gas engine or through an established pipeline for natural gas.

U.S. Pat. No. 5,782,950 describes fermentation of biological waste by a homogenisation, aeration and heating of the mass. The waste is fractionated into a liquid and a solid fraction. The solids is produced into compost. The liquids is fermented by anaerob mesofil and thermofil process with production of biogas. Reject water is recirculated from the biogas reactor to the homogenisation process. Reject water from the biogas reactor is treated in a plant clarification installation. A number of aspects of the invention are not described by this reference. This applies, among other things, to the pre-treatment such as the alkaline hydrolysis, welfare in the animal houses, stripping of ammonia before biogas production, utilization of energi crops, prevention of struvite formation etc. and the use of biogas through a local gas engine or through an established pipeline for natural gas.

U.S. Pat. No. 5,853,450 describes a method to produce pasteurised compost from organic waste and green plant materials. The pH of the organic is increased to 12 and heated to above 55.degree.C. When the green plant material is added pH is lowered to 7-9.5. The mixture is fermented. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

U.S. Pat. No. 5,863,434 describes a method to stabilise organic waste by degradation in a psychrofil anaerob process. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

U.S. Pat. No. 6,071,418 describes a method and a system to treat manure with zone in a way that induces an aerob and an anaerob zone within the material. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

U.S. Pat. No. 6,171,499 describes an improved method to fermentate domestic and industrial waste. The waste is anaerob digested with production of biogas, which is utilized in a gas turbine in combination with natural gas. The fermented material is dehydrated and the sludge is diverted to a incineration plant A number of aspects of the invention are not described by this reference. This applies, among other things, to the pretreatment such as the alkaline hydrolysis, welfare in the animal houses, stripping of ammonia before biogas production, prevention of struvite formation etc. and the use of biogas through a local gas engine or through an established pipeline for natural gas.

WO8400038 describes the production of biogas and degassed and stabilised fertilisers. The thermofil degradation occurs in an inner reactor and the mesofil degradation in an outer reactor. A number of aspects of the invention are not described by this reference. This applies, among other things, to the pre-treatnent such as the alkaline hydrolysis, welfare in the animal houses, stripping of ammonia before biogas production, prevention of struvite formation etc. and the use of biogas through a local gas engine or through an established pipeline for natural gas.

WO8900548 describes the utilization of Ca-ions and Mg-ions in the biogas production. The metal ions inhibit foam production. A number of aspects of the invention are not described by this reference. This applies, among other things, to the pretreatment such as the alkaline hydrolysis, welfare in the animal houses, stripping of ammonia before biogas production, prevention of struvite formation etc. and the use of biogas through a local gas engine or through an established pipeline for natural gas.

WO9102582 describes a plant and a method to produce gas and avoid spreading of harmfull compounds to the surroundings by washing the gas. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

WO9942423 describes a method and a plant to the production of biogas. Fibres and particles from manure is composted and the liquid fraction is fermented anaerobically, stripped for nitrogen. The salts of P and K is utilised for fertilisers by reverse osmosis. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

www.igb.fhg.de/Uwbio/en/Manure.en.html describes a process to produce biogas from manure. From degassed manure the solid fraction is used to produce compost. From the liquid fraction is nitrogen collected and is used as fertilisers. A decanter centrifuge can be used to separate solid components from the mixture. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

rieera.ceeeta.pt/images/ukibo_mass.htm describes a production of biogas by anaerob degradation. A decanter centrifuge can be used in the system. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

www.biogas.ch/f+e/memen.htm describes possibilities to reduce a mixture from solid components. Rotating disc reactor, fixed film reactor, ultrafiltration and reverse osmose is mentioned. A number of aspects of the invention are not described by this reference. This applies, among other things, to the pre-treatment such as the alkaline hydrolysis, welfare in the animal houses, stripping of ammonia before biogas production, prevention of struvite formation etc. and the use of biogas through a local gas engine or through an established pipeline for natural gas.

www.biogas.ch(f+e/grasbasi.htm describes anaerob degradation of silage energi crops and manure with the production of biogas. Two processes is described: 1. Silage energi crops is cut into 1-3 cm and directed to a liquid fraction containing the manure. The mixture i fermented at 35° C. 2. A dry fermentation of manure and silage energy crops without adding further liquid. A number of aspects of the invention are not described by this reference. This applies, among other things, to the pretreatment such as the alkaline hydrolysis, welfare in the animal houses, stripping of ammonia before biogas production, prevention of struvite formation etc. and the use of biogas through a local gas engine or through an established pipeline for natural gas.

www.biogas.ch/f+e/2stede.htm describes the production of biogas. The organic waste is hydrolysed and acidified in a rotating sieve-drum from which the liquid fraction continuos is directed to anaerob degradation of with the production of biogas. A number of aspects of the invention are not described by this reference. This applies, among other things, to the pre-treatment such as the alkaline hydrolysis, welfare in the animal houses, stripping of ammonia before biogas production, prevention of stuvite formation etc. and the use of biogas through a local gas engine or through an established pipeline for natural gas.

SUMMARY OF THE INVENTION

The present invention shall demonstrate a new way of utilizing energy crops, namely through anaerobic co-digestion in farm scale biogas plants with animal manures. The process also includes slurry separation, i.e., refinement of nutrients in the animal manures.

The invention can also be used to co-digest animal cadavers, meat and bone meal etc. with animal manures/energy crops and thus to provide a way of disposing off animal cadavers etc. while at the same time facilitate the production of fertilizers produced from the input of the animal wastes along with the crops, manures etc.

The process design makes it possible to use annual fodder crops such as beets, maize or clover grass, all crops with a higher dry matter yield per hectare than grain cereals. The fodder crops are also beneficial as "green crops" and in crop rotations. The energy potential when using the set aside land for energy crop production shall thus be demonstrated by the present concept.

The central and obvious vision—under a wide variety of circumstances—is that the biogas production based on this concept shall in the future be competitive compared to the use of natural gas and thus be commercial attractive and preferably not subsidised. It is also the vision that the energy production shall constitute a substantial part of the Danish energy consumption, i.e. of the same order of magnitude of the use of natural gas (about 150 PJ annually). In addition to this effect are the benefits in terms of environment, animal welfare and food safety.

Parsby has estimated an energy potential when using energy crops, in particular grain cereals, to 50-80 PJ annually. In the short run this requires an area of 150.000 ha and in the longer run an area of 300.000 ha. However, based on an dry matter yield of 15 tons per ha in beets including tops to be digested in biogas plants the energy potential becomes about 100 PJ annually. The energy from the co-digested manures shall be added to this (about 25 PJ). With the new cultivars of beets the yields of dry matter may substantially exceed the present levels, i.e., yields of the order of 25 tons per hectare.

The core of the invention is a combination of processes which allows increased biogas production, stripping of ammonia and a subsequent optional further use and processing of the digested and stripped remains (the reject water).

It is characteristic that the core of the invention allows further simple and robust processes to be integrated with the core of the invention. A simple and robust energy plant with outstanding energy and economic performances as compared to conventional plants is achieved. The energy plant is further integrated with the management of the animal holdings and the agricultural land. Hence a number of aspects constitute the invention.

In a first preferred aspect the invention may be applied to combat infections and spread of animal microbial and parasitic pathogens such as Campylobacter, Salmonella, Yersinia, Acaris and similar microbial and parasitic organisms to air and agricultural land. The threat to humans of being infected is thus reduced if not eliminated.

In a second preferred aspect the invention may be applied to reduce BSE prions contained in manures, fodder, slaughterhouse waste, flesh and bone meal etc. This is achieved by a combination of pre-treatment and digestion. As part of this aspect, the present invention provides one possibility for handling animal cadavers, slaughter house waste etc. which enables the exploitation of the nutrients contained in the animal cadavers as fertilizers. The reduction and/or elimination of BSE prions contained in animal cadavers, meat and bone meal etc. but also manures, fodder, slaughterhouse waste, etc. during the process of the invention is a prerequisite for this way of handling the waste This is achieved according to the invention by a combination of pre-treatment and digestion. This procedure is an alternative to the present procedure (however now presently prohibited by the EU commission) of processing animal carcasses in central plants and producing various products such as meat and bone meal to be used mainly as animal feed.

In a third preferred aspect the invention may be applied to separate the main nutrients nitrogen (N) and phosphorus (P) from animal manures and refine the nutrients to fertilizer products of commercial quality.

In a fourth preferred aspect the invention may be applied to produce large amounts of biogas from a wide range of organic substrates including all types of animal manures, energy crops, crops residues and other organic wastes.

In a fifth preferred aspect the invention may be applied to ensure optimal animal welfare and health when stabled in the animal houses while at the same time reducing emissions of dust and gasses such as ammonia. This is achieved by flushing or re-circulating reject water through the animal houses.

In a sixth preferred aspect the invention may be applied to benefit from the full range of advantages associated with the various aspects of the invention.

In further preferred aspects any combination of the core invention with any one or more of the other aspects mentioned may be preferred.

Figure 1:
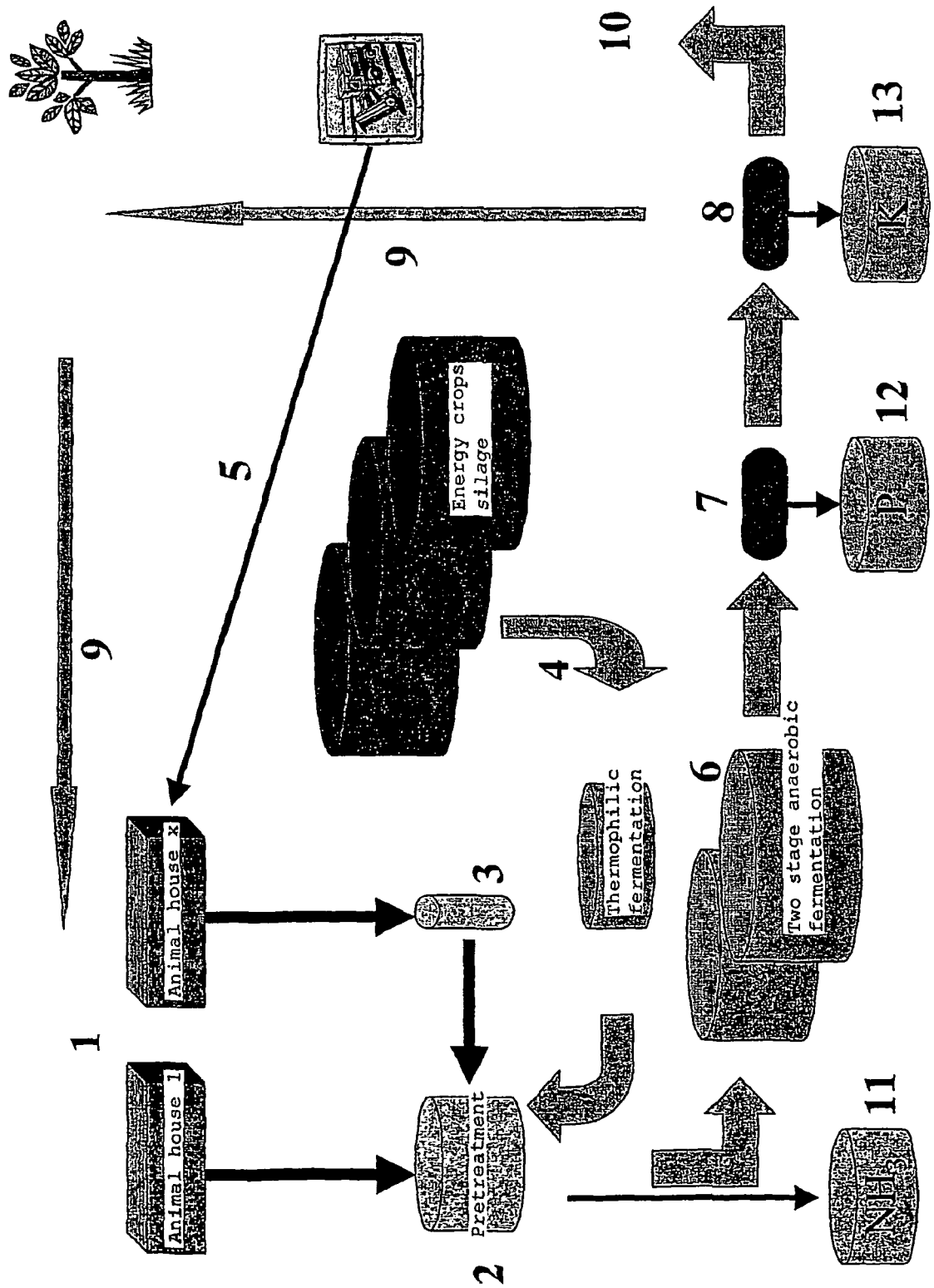
FIG. 1 discloses one preferred embodiment of the present invention. In this embodiment, manure, preferably in the form of a slurry, generated in a house or stable (1) for the rearing of animals, including domestic animals, such as pigs, cattle, horses, goats, sheep; and/or poultry, including chickens, turkeys, ducks, geese, and the like, is transferred to either one or both of a first pretreatment tank (2) and/or a second pretreatment tank (3).

The working principles are that the manure, preferably in the form of a slurry including, in one embodiment, water such as reject water used for cleaning the house or stable, is diverted to the first pretreatment tank comprising a stripper tank, where ammonia is stripped by means of addition to the stripper tank of e.g. CaO and/or Ca(OH)$_2$. However, addition of CaO and/or Ca(OH)$_2$ to the slurry may also take place prior to the entry of the slurry into the first treatment tank or stripper tank.

At the same time as the addition of CaO and/or Ca(OH)$_2$, or at a later stage, the pretreatment tank comprising the stripper tank is subjected to stripping and/or heating, and the stripped N or ammonia is preferably absorbed prior to being stored in a separate tank (11). The stripped N including ammonia is preferably absorbed to a column in the stripper tank comprised in the first treatment tank before being directed to the separate tank for storage.

Organic materials difficult to digest by microbial organisms during anaerobic fermentation are preferably pretreated in a second pretreatment tank (3) prior to being directed to the first pretreatment tank (2) comprising the stripper tank as described herein above. Such organic materials typically comprise a significant amounts of e.g. cellulose and/or hemicellulose and/or lignin, e.g. preferably more than 50% (w/w) cellulose and/or hemicellulose and/or lignin per dry weight organic material, such as straws, crops, including corn, crop wastes, and other solid, organic materials. N including ammonia is subsequently stripped from the pretreated organic material.

In both the first and the second pretreatment tank, the slurry is subjected to a thermal and alkali hydrolysis. However, the temperature and/or the pressure is significantly higher in the second pretreatment tank, which is therefore preferably designed as a closed system capable of sustaining high pressures.

Finally, the slurry having been subjected to a pre-treatment as described herein above is preferably diverted to at least one thermophile reactor (6) and/or at least one mesophile biogas reactor (6). The slurry is subsequently digested anaerobically in the reactors concomitantly with the production of biogas, i.e. gas consisting of mainly methane optionally comprising a smaller fraction of carbon dioxide. The biogas reactor(s) preferably forms part of an energy plant for improved production of energy from the organic material substrate.

The biogas can be diverted to a gas engine, and the energy generated from this engine can be used to heat the stripper tank. However, the biogas can also be diverted into a commercial biogas pipeline system supplying household and industrial customers.

The remains from the anaerobic fermentation, still in the form of a slurry comprising solids and liquids, is preferably diverted, in a preferred embodiment, to at feast decanter centrifuge (7) for separating solids and fluids. One result of this separation is an at least semi-solid fraction comprising almost exclusively P (phosphor), such as an at least semi-solid fraction preferably comprising more than 50% (w/w) P (12). In the same step (7), or in another decanter centrifuge separation step (8), an at least semi-solid fraction preferably comprising almost exclusively K (potassium), such an at least semi-solid fraction preferably comprising more than 50% (w/w) K (13) is preferably also obtained. These fractions, preferably in the form of granulates obtained after a drying step, including a spray drying step or a slurry drying step, preferably comprise P and/or K in commercially acceptable purities readily usable for commercial fertilisers (10). Such fertilisers may be spread onto crops or agricultural fields. The liquids (9) also resulting from the decanter centrifuge separation step, such as reject water, can also be diverted to agricultural fields, they can be diverted back to the stable or animal house, or into a sewage treatment system.

In a further embodiment, the first pretreatment tank may be supplied with organic material originating from silage tanks (4) comprising fermentable organic materials. The divertion of such organic materials to the first pretreatment tank may comprise a step involving an anerobic fermentation such as e.g. thermophilic fermentation tank capable of removing gasses from the silage. Additionally, straws and e.g. crop wastes originating from agricultural fields (5) may also be diverted to stables or animal houses and later to the first and/or second pretreatment tank.

Figure 2:
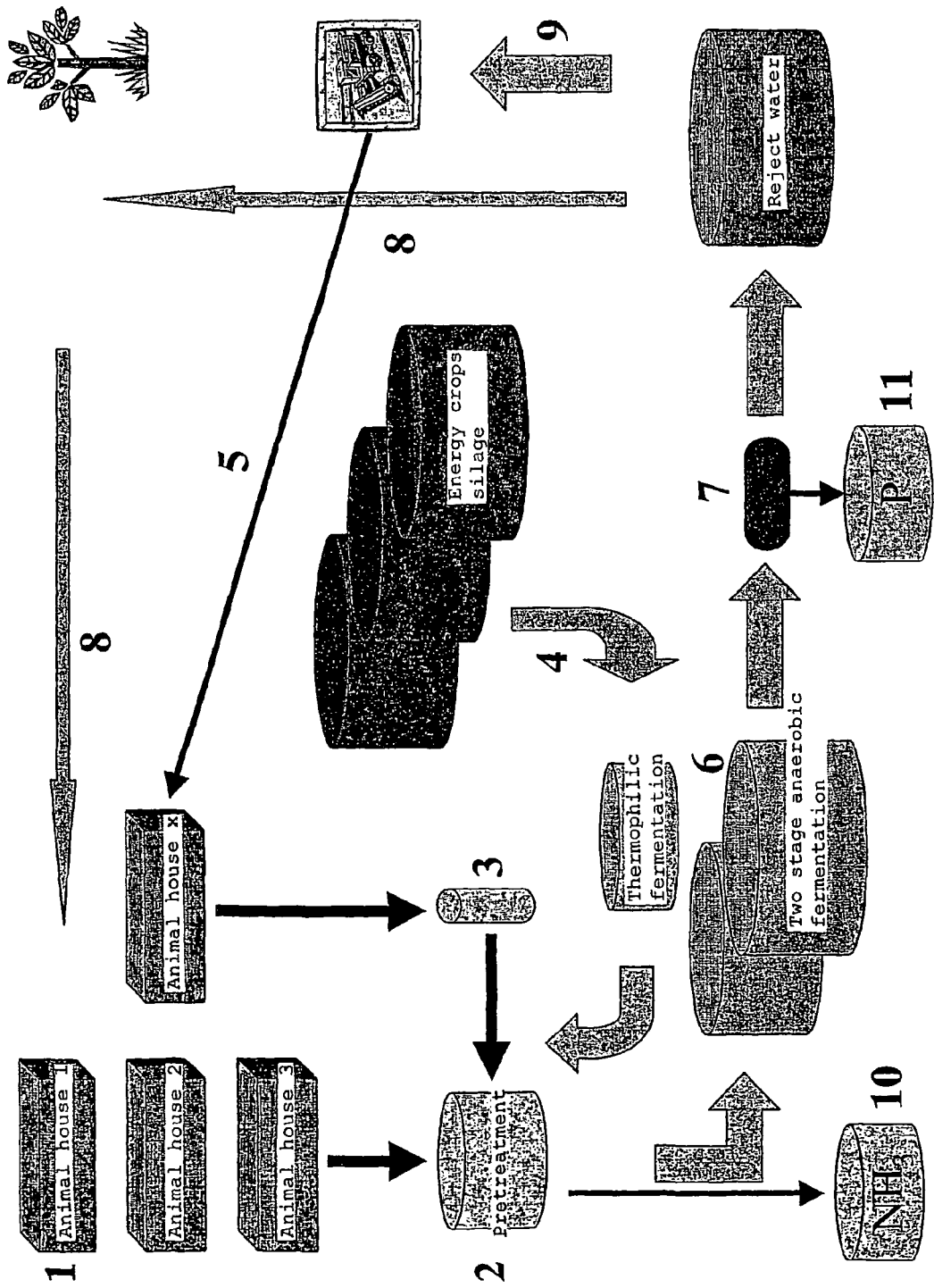

FIG. 2 illustrates an embodiment essentially as described in FIG. 1, but with the difference that only phosphor (P) is collected following decanter centrifuge separation, and water in the form of reject water is collected in a separate tank for further purification, including further removal of N, removal of odours, and the majority of the remaining solids. This may be done e.g. by aerobic fermentation. Potassium (K) may also be separated from the liquids at this stage.

Figure 3:
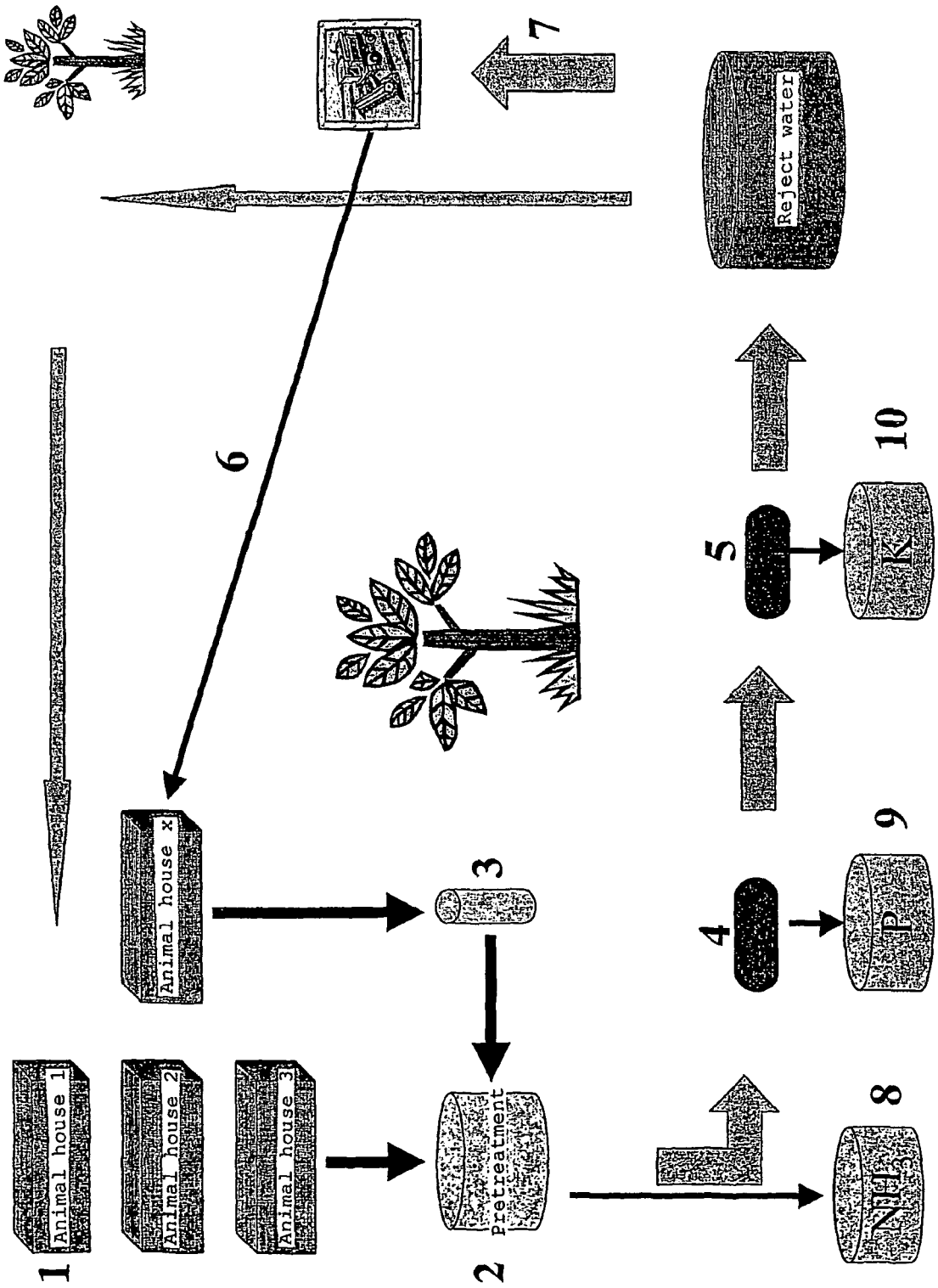

FIG. 3 illustrates an embodiment comprising a simplified approach to the combined biogas and slurry separation system according to the present invention. In this embodiment, no biogas fermentors are used, and the solids resulting from pretreatment in pretreatment tanks one (2) and/or two (3) are subjected to decanter centrifuge separation (4 and 5) following stripping of N including ammonia and collection thereof in a separate tank (8). Separate and at least semi-solid fractions comprising P and K are obtained (9 and 10).

Figure 4:
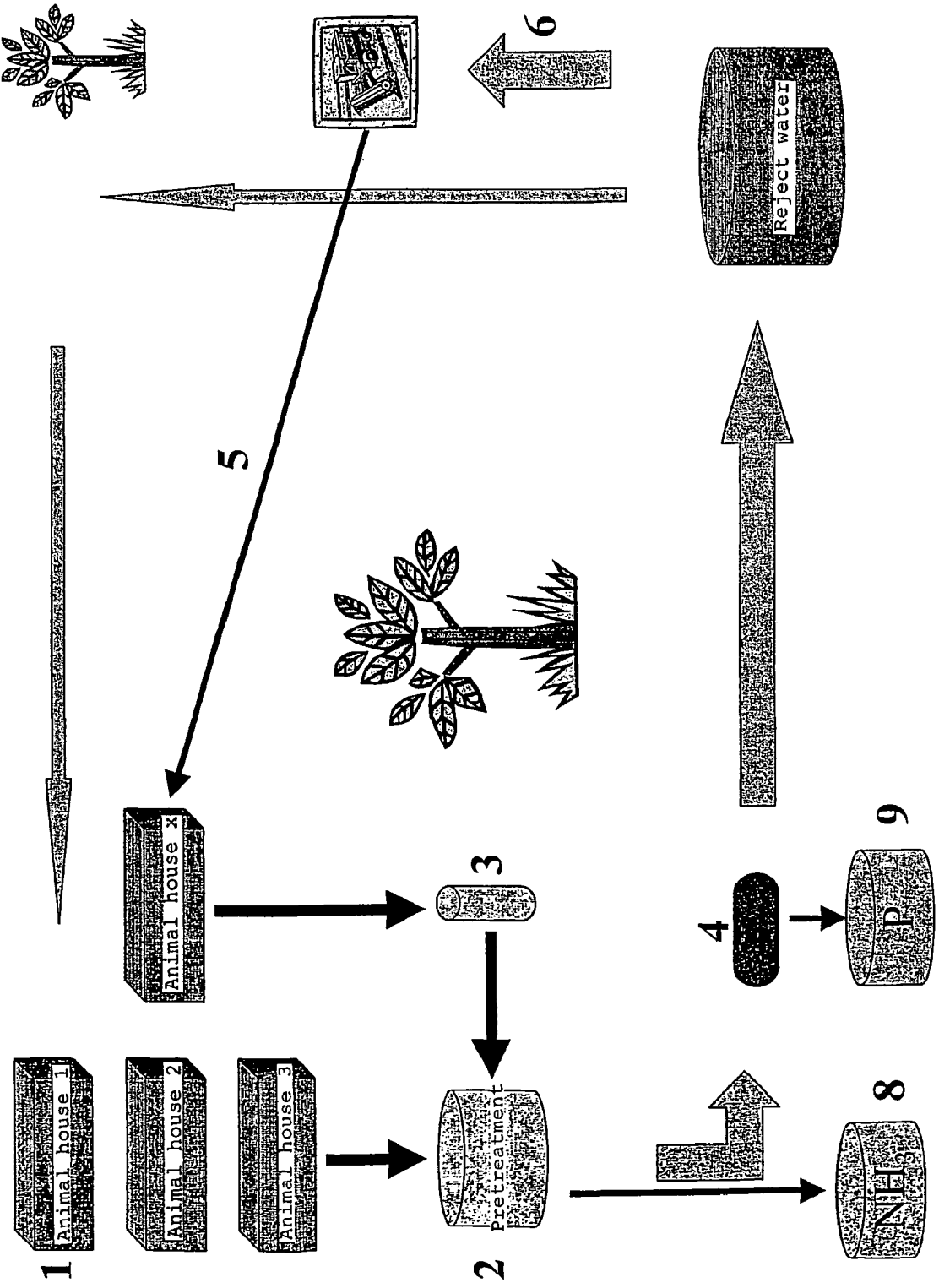

FIG. 4 illustrates an embodiment wherein the potassium (K) is not separated following decanter centrifuge separation as described for the embodiment illustrated in FIG. 3. Further separation of K from the reject water subsequently collected is however possible.

Figure 5:
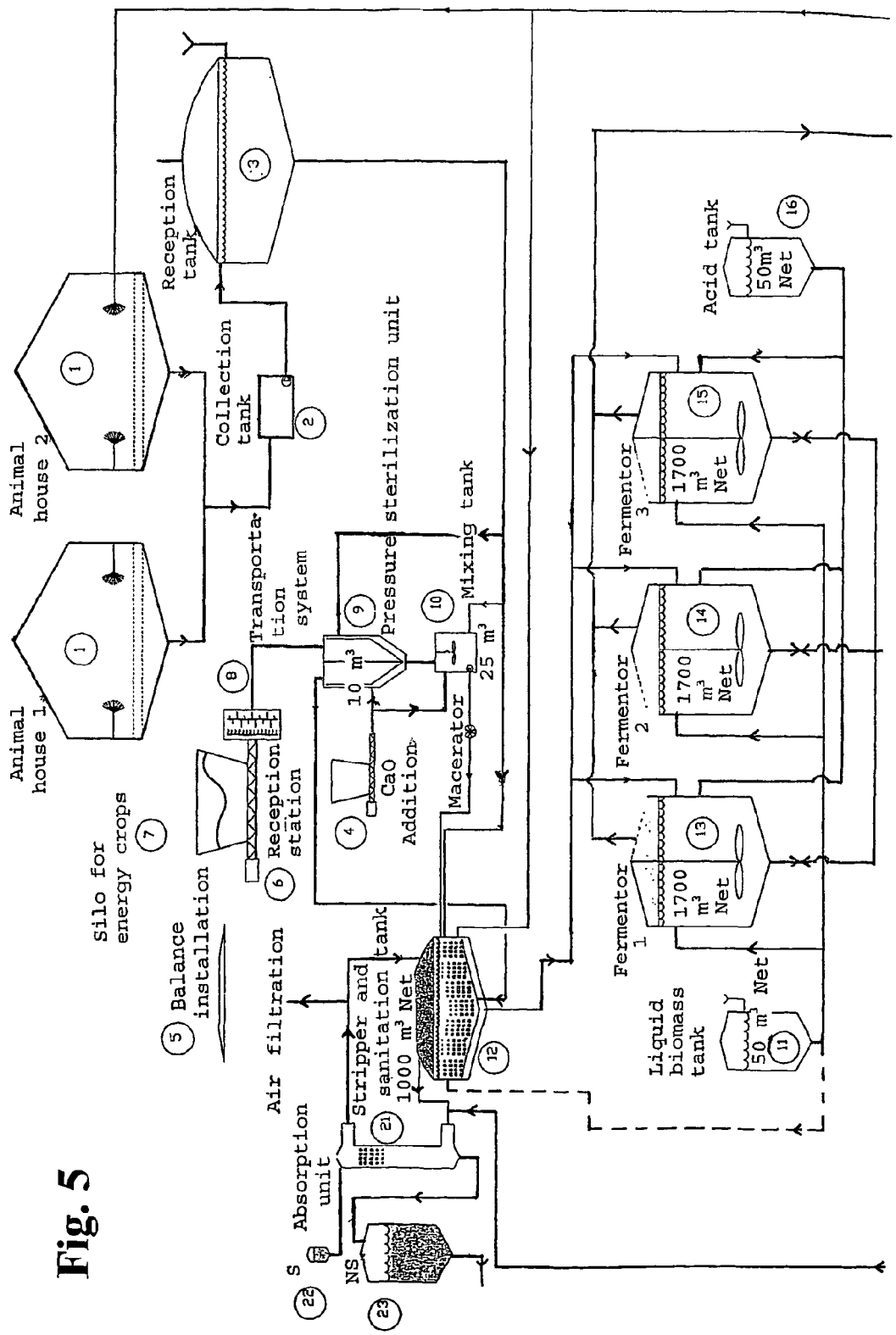
Figure 6:
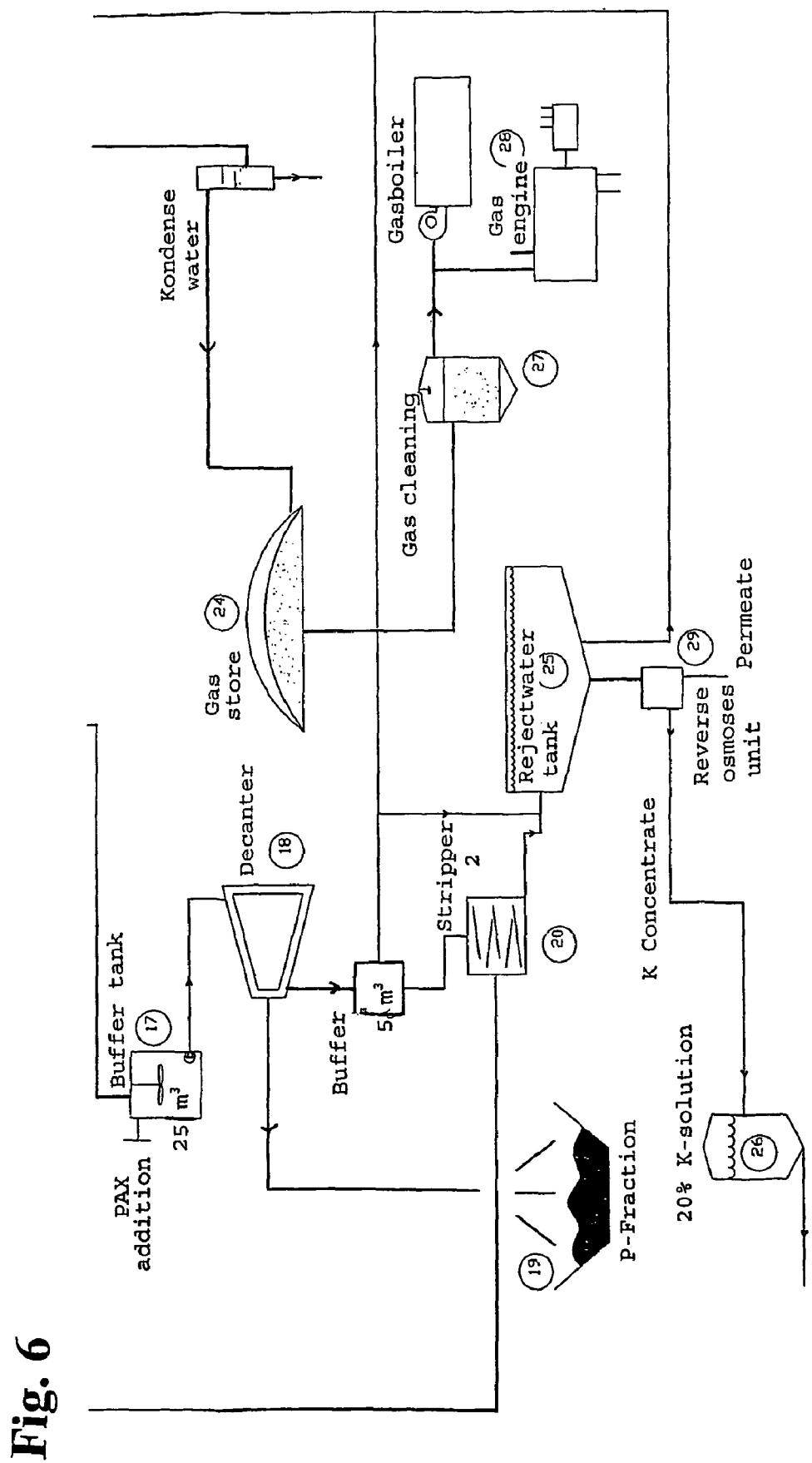

FIGS. 5 and 6 illustrate a preferred embodiment of the system according to the invention. The individual components are described herein in detail.

Further preferred embodiments of the present invention are described in further detail herein below.

DETAILED DESCRIPTION OF THE INVENTION

The present invention pertains to a number of individual aspects as described herein further below.

The First Aspect (Sanitation)

The first aspect includes a system consisting of a first device, a house or stable for the rearing of animals including domestic animals such as pigs and cattle, and/or a second device mainly for stripping of ammonia and pre-treatment of the substrate and/or a third device mainly an energy plant for improved production of energy from the substrate.

The system can preferably consist of an animal house and a stripper tank and a biogas reactor. Additional components can include a device for addition of CaO or $Ca(OH)_2$ to the slurry, an absorption column operated on the basis of e.g. sulphuric acid, a storage tank for the ammonia concentrate, and a storage tank for digested slurry.

The produced biogas can desirably be used for production of current and heat in a gas motor and generator, the current preferably being sold to a net and the heat preferably used for heating of e.g. slurry and/or animal houses. The energy plant according to the invention has an outstanding performance in terms of the energy production per unit substrate treated in the plant. The outstanding performance is achieved by a combination of pre-treatment of the substrate to be digested, whether animal manures or other organic substrates, with stripping of ammonia from the substrate before anaerobic digestion.

The advantages associated with the present invention are described in more detail herein below. One central aspect of the sanitation aspect of the invention is a pretreatment comprising—alone or in combination—a number of individual pretreatment steps described in detail in the following:

Pre-treatment of slurry following removal from the animal houses can include any one or more of the following steps: 1) ammonia stripping, 2) hydrolyses of organic matter, 3) sanitation of the slurry, 4) reduction of foam formation, 5) flocculation, 6) precipitation of P, and 7) prevention of struvite formation.

The working principles are that slurry is diverted from the first device to a stripper tank where ammonia is stripped by means of addition of CaO or $Ca(OH)_2$, stripping and heat and absorbed in a column before stored in a tank. At the same time the slurry is subject to a thermal and alkali hydrolysis, preferably by using a lime cooker. Finally the pre-treated slurry is diverted to the third device, consisting of one or two thermopile/mesopile biogas reactors, where the slurry is digested anaerobically under the production of biogas, i.e. gas consisting of mainly methane with a smaller fraction of carbon dioxide. The biogas is diverted to a gas engine and the heat from this engine is used to heat the stripper tank. The current produced is sold to the net.

As straw and possibly also sawdust is a significant fraction of deep litter from cattle and poultry holdings, there is a need for a specific pre-treatment of these manures before optimal use as substrate for methane production in biogas plants. Lime pressure cooking represents one preferred pre-treatment method in this respect. Deep litter treated by this technology can thus be made available for methane production in a more efficient way and result in an increased biogas production. Additionally, it is assured that uric acid and urea dissociates to ammonia and that proteins and other substances are dissolved. It is hereby ensured that the inorganic nitrogen from the deep litter can be collected in the N-concentrate by the ammonia stripping process.

The availability of the N in the deep litter and poultry manure to agricultural crops is therefore substantially increased. It is estimated that the potential utilization efficiency can be increased to about 90% as is the case for the other manures treated in the biogas and slurry separation plant according to the present invention.

Alternatively, it may be appropriate to digest the poultry manure in the first thermo- or mesopile reactor before passing it to the stripper tank. This depends on the quality of the manure and to which degree the uric acid dissociates due to the two different treatments. Experience gained after some working time of the plant shall clarify this. It is important to stress the versatility of the plant which allows all types of manure and energy crops to be treated.

The technical construction is relatively simple because a screw conveyor equipped with a macerator, all made of rust- and acid proof steel, conveys the biomass into a lime cooker where the mass is heated by a steam injection to 180-200° C. The pressure becomes 10-16 bar during the 5-10 minutes necessary for the mass to be treated.

The unit to be constructed shall be able to produce temperatures and pressures in the temperature interval of 100-200° C. Hereby it is possible to adjust the treatment to different biomasses to be digested in the plant according to the invention under due consideration to use of energy, tar formation and technical parameters.

Foam formation represents a common problem in biogas plants. One preferred choice for controlling foam formation in biogas plants, in particular when supplied with large amounts of biomass from e.g. energy crops, is rape oil, which in addition to the effect of foam control also is a substrate for methane gas formation. Ca-ions are also very efficient in controlling foam as are many salts. One preferred foam controlling measure of the present invention is $Ca(OH)_2$ and/or CaO in addition to its other effects mentioned earlier. Supplementing the slurry with Ca-ions is also believed to stimulate the formation of flocks and the bacterial adhesion to organic particles and thus the performance of the anaerobic digestion.

Accordingly, if additional foam control and/or flocculation is needed in the process because of a very high gas production the fermenters may be supplied directly with Ca and/or rape oil. The addition of $Ca(OH)_2$ or CaO will also lead to precipitation of bicarbonates as $CaCO_3$. This reduces the $CO_2$ concentration in solution and in the gas phase and contribute to the reduction of foam formation through reduced carbon dioxide emissions.

Addition of $Ca(OH)_2$ or CaO in connection with stripping of ammonia and sanitation of the slurry will also lead to precipitation of orthophosphate, i.e. dissolved $P(PO_4^-)$. These P-particles may be suspended in the slurry as well as other flocks. The use of Ca will also lead to a limited reduction of chemical oxygen demand (COD), which means that Ca precipitates other salts than just the orthophosphate.

It is believed that—irrespective of the chemical differences between various organic waste products, a simple heat treatment and in particular heat treatment in combination with alkali hydrolysis will lead to an increased gas yield. Furthermore, a combination of high temperatures and high pH during pre-treatment is believed to result in a more effective sanitation of the organic material as compared to anaerobic digestion alone, whether thermofile or mesofile.

It should be noted that in the Statutory Order no. 823 from the Danish. Ministry of Environment and Energy, it is laid down that a controlled sanitation consists of 1 hour residence time at 70° C. In view thereof, a treatment according to preferred embodiments of the invention consisting of one week residence time at 70° C. before two subsequent anaerobic digestions (thermo- or mesofilic) is believed to completely eliminate all known veterinary and/or human microbial and zoonotic pathogens. Preferably, BSE prions are also eliminated or at least significantly reduced in number.

The overall result is that all infectious organisms in the slurry are eliminated and therefore not spread to the environment when the manure is applied to land. This also makes it possible to flush the first device (the animal houses) with the digested slurry in order to maintain the sties etc. clean. Cross infections among animals are thus prevented. It also allows further use of water to rinse animals and sties, air exhausts etc. with the effects of preventing emissions to air of odour, dust and infectious agents. This is possible because the slurry with additional water shall not be stored till periods where land speeding is permitted. The slurry without N may be spread to land throughout the year.

However, in the first aspect it is the pre-treatment and thus the sterilization of the slurry which is preferred in order to to allow subsequent spreading onto agricultural fields.

It will be clear that the present invention relates to a variety of different aspects, which constitute, individually or in combination, patentable inventions in their own right. The below section contains a description of various individual parts (components) of one aspect of the present invention. An overview of the components are given in FIGS. 5 and 6.

It will be understood that selected components can form the basis for other aspects of the present invention. The invention shall in no way be limited to the combination of the entire list of components described herein below. It will be clear from the description when other aspects of the invention are related to only some of the components described herein below. Non-limiting examples of such aspects includes devices for concentration of N (nitrogen) and/or P (phosphor) and/or K (potassium); energy generation based on the components of stripper tank, lime cooker and fermentor; and animal welfare/reject water processing.

It will also be understood that the below aspects related—among other things—to the aspect of sanitation, does not necessarily have to comprise all of the components illustrated below. Aspects related to sanitation are also understood to comprise a combination of only some of the components described herein below.

Animal Houses

The animal houses (Component number 1) serves to provide an optimal food safety and food quality, an optimal animal welfare and working conditions for the labour personal in the housings, an optimal slurry management, suitable for treatment in the GreenFarmEnergy plant, and a reduction of emissions to the external environment to a minimum (ammonia, dust, odour, methane, dinitrogen oxide and other gasses).

The housing system can consist of one or more early weaning houses with a total of 10 sections designed to produce 250 livestock units annually. Each section houses e.g. 640 piglets (7-30 kg) or 320 slaughter pigs (30-98 kg).

An amount of about 10.000 m3 slurry can be expected to be produced annually. In addition to this volume an amount of 5-10.000 m3 process water shall be recycled through the houses. The following main conditions shall preferably be met by the housing system:

1) Two-climate system: The sties shall preferably be designed as two-climate systems. The back end of the sties shall be equipped with an adjustable coverage providing an opportunity for the pigs to choose between a relatively warm environment under the covering and a relatively cold environment in the rest of the sty. The temperature difference shall be in the range of 5-10 deg. C.

When the piglets have grown to around 30 kg the coverage shall be used to allow for generally colder temperatures in the animal house as such. The pigs may keep warn under the coverage. By allowing for colder temperatures it is possible to increase ventilation also during colder ambient periods.

2) Occupation: The pigs are preferably offered straw from an automate. The searching and digging behaviour is hereby stimulated, because they shall pick out the straw from the automate by themselves. The straw serves also as an energy source in the energy plant.

3) Heating: Heat from the energy plant is preferably recycled to the animal houses. The heat can be provided by two separate circulation systems. One is located under the covering to 30-35° C., which provides the pigs with a comfortable microclimate, keeps the floor dry and reduces bacterial growth on the floor. The second provides heat to the overall airspace in the house via pipes along the walls of the house. The second circulation is coupled to the ventilation control.

4) Showers: Showers are preferably established over the slats. which covers ¼ of the total floor area. This motivates the pigs to manure on the slats. as opposed to the solid floor. The shower water will flush the manure into the canals preventing malodour, ammonia losses etc. The clean solid floors substantially reduces the possible infections form pathogens in the manure as *Salmonella, Lawsonia* etc.

5) Flushing: The manure canals are preferably flushed several times a day. It is provided by flushing of canals with process water from the energy plant. The manure is diverted to a central canal through a valve.

6) Canal design: The surface of the manure is reduced by use of V-shaped canals and an optimal flushing of the canals are achieved at the same time. This is central for the reduction of emissions from the animal houses.

7) Ventilation: The ventilation is designed so that 20% of the maximum ventilation is diverted down under and through the slats. into central ventilation shack. between the double V-canals. In 60-80% of the year 20% of the maximum ventilation is sufficient to provide amble ventilation.

8) Feeding: Foodstuff is provided by a wet feeding equipment which provides fodder ad libitum.

Slurry Collection Tank

The function of a slurry collection tank (Component number 2) is to collect slurry form the daily flushings of the animal houses and to work as a buffer before pumping to the main reception tank. The slurry is diverted to the collection tank by means of gravitation. The volume can be anything appropriate, such as e.g. 50 m$^3$. The tank can be made of concrete and it can be placed below the floor in the animal houses so that the slurry form the houses can be diverted to the collection tank be means of gravitation.

Main Reception Tank

Slurry from the collection tank is preferably pumped to the main reception tank (Component number 3). Other types of liquid manure/waste may also be added to the reception tank from other farms/plants. Options are mink slurry, cattle slurry, molasses, vinasses, silage etc. This is transported to the reception tank by lorry and is loaded directly into the reception tank. The volume/capacity is anything appropriate, such as e.g. about 1.000 m$^3$. The level in the stripper tank preferably controls a pump, which pumps slurry from the reception tank. The dose adjustment can be manual or automatic. The maximum capacity can be anything appropriate under the circumstances.

CaO Addition

When slurry is being pumped from the reception tank 1 to the stripper tank, lime is added to the slurry in order to increase the pH. The lime addition manifold is preferably adjusted to add 30-60 g CaO/kg TS. The lime is preferably supplied as a powder which can be blown into the silo from the lorry. The volume/capacity of the silo can be e.g. about 50-75 m$^3$. The dose of 30-60 g/kg TS corresponds to app. 6-12 kg CaO per hour with a slurry capacity of 3.5 m$^3$/h with 6% TS.

When added directly to the slurry (6% TS), the lime dose is about 60 g/kg TS yield (about 8.8 kg CaO per hour). It is however preferred to add the lime directly to the alkali pressure sterilazation and hydrolysis unit. When lime is added directly to the pressure unit (the E-media hold 2G-70% TS), the lime dose is about 30-60 g/kg TS. 60 g 1 kg d.m. equals about 342 kg CaO per batch, while 30 g/kg d.m. equals about 171 kg CaO per batch.

Balance Installation

The balance (Component number 5) shall preferably weigh the incoming E-media (energy containing organic material). The suppliers will preferably specify the type of media which is supplied to the plant, i.e. deep litter, energy crops etc. of various sorts.

The specification shall be made by selecting the relevant E-media on a control panel. According to the suppliers panel registration, the weight of received E-media incl. specification of media is recorded.

The control thus specifies for each E-media (see alkali hydrolysis):
  Energy potential
  The required heating time
  The required retention time Reception Station for Deep Litter and Energy Crops The reception station (Component number 6) shall receive deep litter from e.g. poultry or other animals as well as energy crops. The station is preferably a large silo equipped with several screw conveyors in the floor. The lorries will empty their load of E-media directly into the silo. The volume/capacity can be anything appropriate under the circumstances, such as e.g. a yearly capacity of E-media (about 51.5% TS) of about 9.800 tonnes. The volume of the silo can be from several cubic meters to about 100 m$^3$, corresponding to three days capacity (65 h). The materials are preferably concrete/steel.

Silo for Energy Crops

The silo for energy crops (Component number 7) serves to provide storage means for energy crops. The crops are preferably conserved as silage. The volume/capacity can be e.g. from about 5.000-10.000 m$^8$. The silo can be a closed compartment from which silage juice is collected and pumped to the reception tank.

Transport- and Homogenisation System for Deep Litter and Energy Crops

The transport- and homogenisation system (Component number 8) for deep litter and energy crops preferably receives E-media from the screw conveyors in the floor of the reception station. The E-media can be transported by additional screw conveyors to the cooking units and at the same time preferably macerated by an integrated macerator. The volume/capacity can be anything required under the circumstances including about 1.5 m3 E.media/hour, or 8.200 tonnes of E-media/year. The capacity of the transport-homogenisation system is preferably not less than about 30 m3/hour. Three fundamental parameters shall control the addition of E-media, i.e. volume, weight per volume, and time. From these parameters volume per unit time, time and thus total volume and weight shall be established.

Alkali Pressure Sterilization and Hydrolysis Unit

The alkali pressure sterilization and hydrolysis unit (Component number 9) shall serve two main purposes, i.e. firstly elimination of microbial pathogens in the E-media in particular in deep litter from various poultry or other animal productions and secondly, at the same time hydrolyse structural components of the litter in order to render them available for microbial degradation in the fermentors.

The unit shall also preferably eliminate or at least substantially reduce BSE-prions if present in waste introduced into the plant. Such waste include flesh- and bone meal, animal fats or similar produce from the processing of animals not used for consumption.

Filling of the pressure sterilizer is provided by the transport- and homogenisation system, which transports E-media into the according to type of E-media as defined on the balance installation.

The pressure cooking unit consists of two identical units, i.e., two elongated pipe-like horizontal chambers with a central screw. The two pipes are fastned one on top of the other in order to provide for easy loading of the lower pipe. The units are covered by a hollow cape on the downwards side. The cape shall divert heat to the media from steam under the cape.

Lime is added to the upper cooking unit from the CaO silo, i.e., 342 kg per batch.

The lower pipe receives pre-heated E-media from the upper unit.

The lower unit is emptied into a small mixertank containing 25 m$^3$. Here the E-media is mixed with slurry from the reception tank 1, the mixture is subsequently pumped into the strippertank.

The CaO tupe contains a by pass so that CaO can be added directly into mixing container under the two pipes. The mixing chamber is used for mixing sterilized E-media and raw slurry from the reception tank to provided a homogeneous biomass and to reuse the heat of the E-media.

The central process parameters are dry matter content of the E-media, temperature, pressure and pH. From a wide range of possible combinations the optimal parameter setting is a temperature of 160° C., pressure of 6 bar, dry matter content og app. 30%, and pH of app. 12.

The retention time in the sterilization unit consists of several phases: 1. Filling time; 2. Preheating time in the upper pipe; 3. Heating time in the lower pipe; 4. Retention time at the selected temperature and pressure; 5. Pressure release time; 6. Emptying time, and 7: CIP time The filling phase consists of the time required to transport the E-media into the pressure sterilizer and mix it with the added slurry. The filling time shall be app. 10 min. After filling the E-media shall be heated to 160° C. at 6 bar. Preheating takes place in the upper pipe and final heating in the lower pipe. Heating time is expected to be app. 30-40 min.

The retention time at the desired temperature and pressure shall be app. 40 min (at 160° C. and 6 bar).

Pressure release time app. 10 min. The pressure is released into the stripper tank.

Emptying is achieved by running of the screw conveyors.

CIP time. Cleaning performed on occasion, generally not necessary.

The volume of the pressure cooker is 10 m$^3$ per unit, and the degree of filling is app. 75-90%. The volume of the mixing container is 25 m$^3$.

An example of running conditions are illustrated below.

|  | Range | Selected | Units |
| --- | --- | --- | --- |
| TS | 10-30 | 30 | % of total weight |
| Temperature | 120-160 | 160 | ° C. |
| Pressure | 2-6 | 6 | Bar |
| PH | 10-12 | 12 | pH |

At the panel for suppliers where E-media are registered the following shall preferably be defined for the control of the sterilization unit: Weight, volume and sort of E-media. It is thus possible to define for each E-media transported to the pressure cooker the:

- Energy potential for each E-media
- Necessary heating time
- Necessary retention time
- Necessary mixing time with the slurry
- Necessary energy use depending on E-media
- Degree of filling, signal from radar/microwave gauge
- Empirical based values depending on visual monitoring by the operator Mixing Tank for Pressure-Sterilized E-media and Raw Slurry Following sterilization and hydrolysis in the pressure unit, the treated biomass is allowed to expand into a mixingtank (Component number 10) preferably located below the pressure unit. Excess pressure (steam) is released into the strippertank in order to collect ammonia and transfer heat to the stripper tank biomass before expansion into the mixertank.

The purpose of the mixertank is to mix cold raw slurry from the reception tank with hot sterilized E-media in order to obtain heat transfer (re-use of heat) and mixing of the two media.

The volume/capacity is e.g. about 25 m$^3$. Any suitable material can be used, including insulated glasfibre. The working temperature is typically about 70-95° C.

Tank for Liquid Biomass

The liquid biomass contained in the tank for liquid biomass (Component number 11) shall be use to ensure sufficient biogasproduction during the start up phase of the whole plant. However, it can also be used occasionally, when such liquid biomass is available. Liquid biomass include e.g. fish oil, and animal or vegetable fats. Vinasses and molasses can also be used, but this is not preferred because of the relatively high water content and thus low potential energy content per kg product.

The volume/capacity is typically about 50 m$^3$, and a suitable material for the tank is stainless steel. The contents of the tank is preferably liquids and solids having a particle size of max. 5 mm. Stirring as well as a heating system for temperature control is preferably provided, as are feeding pump(s) to the fermentor(s). The temperature shall preferably be min. 75° C. so that oily or fatty biomass can be pumped into the fermentor(s).

Stripper and Sanitation Tank

The stripper and sanitation tank (Component number 12) preferably receives the following media:

- Slurry from reception tank 1 and/or
- E-media from the pressure cooker, and/or
- Possibly liquid biomass from biomass liquid tank, and/or
- Reject water from decanter or possibly after K-separation.

The purpose of the tank is to regenerate heat used in the pressure cooker by heating the slurry from reception tank 1, to mix the E-media with slurry and hence to produce a homogeneous feed to the fermentors, to control pH before feeding to fermentors, and to sanitise the slurry.

The stripper and sanitation tank strips ammonia, step I, and the gas is diverted to an absorption column which is common to the final stripper process, step II. Microbial pathogens are eliminated and the media/slurry is prepared for anaerobic digestion.

One presently preferred shape of the stripper and sanitation tank is:

Bottom/Floor
- With insulated concrete cone, directed downwards angle 20 degrees
- Impaired stirring/sand is removed from the floor or according to the mammut pumping system
- A sand filter is placed in the bottom, which can be emptied throughout an external pipe connection. It will also be possible to empty the tank through the filter Top/Ceiling
- With cone construction of sandwich insulated Isofatalic Polyesters (Encapsulated Foam). Cone angle is approximately 10 degrees.
- Mounted water drizzle system to avoid the production of foam from the stirring process and the process in common.
- A slow running stirring system is placed on top of cone to to ensure the optimal homogenisation,-optmal vaporation of the ammonia, and optimal distribution of heat in the media.
- The ammonia is transported through wet air in a pipe to the absorbing unit Side/Wall
- With cylinder construction of sandwich insulated Isofatalic Polyesters (Encapsulated Foam).
- Mounted approximately 600 meters of heating ⅝" pipes in a cylinder ring shape inside the tank to heat up the media
- Mounted some temperature transmitters to regulate the heating process
- Mounted a pH-measuring instrument to regulate the acid supply to the media
- Outside cylinder wall at the bottom is mounted a insulated valve/pumping room
- An ammonia steam diffuser is placed in the middle of the tank. The ammonia steam generated in the alkali sterilisation and hydrolysing unit is diffused into the media.

Volume/Capacity: The cylinder wall has an inside diameter of about 12 m and a height of 9 m. This means a tank handling volume of approximately 1.000 m$^3$ the bottom cone included.

The hydraulic retention time for slurry and E-media is about 7 days, and the absolute minimum retention time is about 1 hour.

In one preferred embodiment, the bottom is basically made of concrete, arming iron and pressure proof insulation. The surface in contact with media is coated with isofatalic Polyester to avoid corrosive damaging of the concrete and arming iron. All pipes mounted in the bottom is either polyester or stainless steel. The top and bottom is basically a construction of sandwich insulated Isofatalic Polyesters (Encapsulated Soap). All pipes mounted is either polyester or stainless steel.

Other Components
- The stirring element is made of stainless steel
- The heating elements is made of coated mild steel and/or stainless steel
- All other components placed inside the tank is made of stainless steel In one preferred embodiment, default parameter values for stripping of ammonia from slurry in this system are: Temperature of about 70° C.; pH of about 10-12; liquid gas ratio of <1:400, 1 week operation, and more than 90% affectivity is achieved.

An example of conceivable running conditions are listed below:

| Media: | All sorts off liquid animal manure and pressure sterilized solid or liquid E-media, various liquid organic wastes, CaO. |
|---|---|
| Running temperature: | 70-80° C. |
| Running gas combination: | 80% $NH_4$, 15% $CO_2$, 3% $O_2$, 2% other gases |
| Insulation k-value: | 0.20 $W/m^2K$ |
| Running Max. Pressure: | +20 mbar abs. (No vacuum) |
| Max. viscosity in media: | 15% TS |
| Base/Acid-range: | 5-10 pH |
| Abrasive rudiments in Media (Ex. Sand): | 1-2% |
| Max. temperature in heating elements: | 90 degrees celcius |
| Max. effects in heating elements: | 600 kW |
| Transmission effect: | 7.5 kW/20-25 rpm. |

The stripper and sanitation tank supplies the fermentor(s) with treated material for fermentation. In a timed process the material will be transported to the fermentors. The demand of material depends on the digestion process in the fermentors. One, two, three or more fermentors can be employed.

The stripper and sanitation tank is regularly filled with slurry and E-media from the alkali pressure process. Finally, to obtain a dry matter of ~15% (15% TS). Some level switches regulate the content in the tank. A TS-measuring unit regulates the content of TS. Every 1 hour after filling of slurry and E-media it is possible to pump E-media to the fermentor(s).

The top of the stripper and sanitation tank is preferably ventilated through an ammonia-absorbing unit (Step I), and a pH-measuring unit regulates the need for CaO.

The temperature of the E-media is regulated through temperature transmitters.

A timed process can optionally pump water/slurry into the drizzle system to prevent production of foam.

Fermentors for Biogas Production

Digestion of the biomass is provided by a multi-step fermentor system preferably comprising three fermentors (Components 13, 14 and 15). Systems with fewer as well as more fermentors can also be applied.

The fermentors are preferably connected to achieve maximum flexibility and optimum biogas production. The fermentors shall be planned for routinely running at termofile (45-65° C.) as well as mesofile (25-45° C.) temperatures.

The digestion process can be optimised in terms of organic loading rate, retention time, and maximum digestion (min. 90% of VS). Heat spirals are included in order to heat the biomass to the preferred running temperature.

A top fastened slow running stirrings system ensures optimal homogenisation and distribution of heat in the biomass.

Regulation of pH is possible through addition of an organic acid (liquid) in necessary quantities.

The fermentors preferably receives the following media:
E-media from the stripper and sanitation tank
Liquid biomass from the liquid biomass tank
Acids from the acid tank The specific shape of the tank can in one preferred embodiment be:

Bottom/Floor
With insulated concrete cone, directed downwards angle 20 degrees
Impaired stirring/sand is removed from the floor or according to the mammoth pumping system
A sand filter is placed in the bottom, which can be emptied throughout an external pipe connection. It will also be possible to empty the tank through the filter Top/Ceiling
With cone construction of mild steel. Cone angle is approximately 10 degrees
Mounted water drizzle system to avoid the production of foam from the stirring process and the process in common
A slow running stirring system is placed on top of cone to ensure the optimal homogenisation, and optimal distribution of heat in the media.
The biogas is transported through wet air in a pipe to the gasbag.

Side/Wall
With cylinder construction of mild steel.
Mounted approximately 600 meters of heating 5/4" pipes in a cylinder ring shape inside the tank to heat up the media
Mounted some temperature transmitters to regulate the heating process
Mounted a pH-measuring instrument to regulate the acid supply to the media
Outside cylinder wall at the bottom is mounted a insulated valve/pumping room The volume/capacity of each tank canhave any suitable net volume, including a net volume of about 1.700 $m^3$.

The materials for the fermentors can e.g. be as specified below:

Bottom
The bottom is basically made of concrete, arming iron and pressure proof insulation
The surface in contact with media is coated with Isofatalic Polyester to avoid corrosive damaging of the concrete and arming iron
All pipes mounted in the bottom is either polyester or stainless steel Top and Wall
The top and wall is basically a construction of mild steel
All pipes mounted is either polyester, stainless steel or mild steel Other Components
The stirring element is made of mild steel
The heating elements is made of mild steel
All other components placed inside the tank is made of stainless steel or mild steel The running conditions can be any conditions suitable, including

| Media: | All sorts off animal manure, primarily pigs slurry. Macerated energy crops. Some sorts of organic waste, CaO, organic Acids |
|---|---|
| Running temperature: | 35-56° C. |
| Running gas combination: | 65% $CH_4$, 33% $CO_2$, 2% other gases |
| Insulation k-value: | 0.25 $W/m^2K$ heatloss is estimated to 10 kW |
| Running Max. Pressure: | +20 mbar abs. (No vacuum) |
| Max. viscosity in media: | 12% TS |
| Base/Acid-range: | 5-10 pH |
| Abrasive rudiments in media (Ex. Sand): | 1-2% |
| Max. temperature in heating elements: | 80 degrees celcius |
| Max. effects in heating elements: | 600 kW |
| Transmission effect: | 7.5 kW/20-25 rpm |

The digestion shall be run at about 55° C. Heat loss is estimated to about 10 kW. The biomass in the tank is can be heated from 5° C. to 55° C. during 14 days, and the possibility of addition of acid for adjustment of pH.

Tank for Organic Acids for pH Adjustments in Fermentors

A tank for organic acids (Component number 16) for pH adjustments in the fermentor(s) is preferably also provided.

Buffer Tank for Degassed Slurry Before Decanter

Following digestion of the biomass in the fermentors the degassed biomass is pumped to a small buffer tank (Component number 17) before being subjected to separation in the decanter.

Decanter Installation

The function of the decanter installation (Component number 18) is to extract suspended solids (ss) and P from the biomass.

The decanter separates the digested biomasse into the two fractions i) solids, including P, and ii) reject water.

The solids fraction contains 25-35% d.m. App. 90% of the ss. and 65-80% of the P-content of the digested biomass is extracted. In case of addition of PAX (Kemira Danmark) to the buffer tank before separation in the decanter, app. 95-99% of the P can be extracted. The solids fraction is transported to containers by means of a shaft less screw conveyor.

The rejectwater contains 0-1% ss and dissolved K. The ss depends on the addition of PAX. The principal component of the reject waters is dissolved K which amounts to app. 90% of the original K-content in the biomass. The reject water is pumped to the reject water tank.

P-Fraction Transport System and Treatment

From the decanter installation the solid matter fraction (routinely called the P-fraction) can be transported to a series of containers by means of conveyor screws and belts forming a P-fraction transport system (Component number 19).

A common conveyor band transports P-fraction to a storage where it is stacked into miles, covered with a compost sheet and allowed to compost. The composting process further dries the P-fraction and the d.m.-content thus increases to 50-60%.

Second N-Stripping Step

Efficient stripping of ammonia from the reject water is preferred, and a residual level of about 10 mg $NH_4$—N/ltr or less is preferred.

The second stripping step is preferably carried out by using a steam stripper operated at ambient pressure. The stripper principle benefits form the different boiling temperatures of ammonia and water. At temperatures close to 100° C. extraction of ammonia is most efficient. The use of energy in order to heat the feed is an essential running parameter. The stripper unit shall therefore preheat the feed before entering the stripper column to close to 100° C. This is provided by use of steam (or possibly warm water and steam) from the motor-generator unit in a steam-water heat exchanger.

When heated the feed enters the stripper column and percolates over the column while at the same time being heated to the running temperature by a counter current of free steam. The steam/ammonia gas is subsequently condensed in a two step condensator.

From the floor of the column the water now free of ammonia is pumped to a level controlled exit pump.

The stripped ammonia is diverted to the bottom of a two-step scrubber condensator where the ammonia gas is condensed primarily in a counter current of cooled ammonia condensate. The ammonia gas not condensed are subsequently condensed in a counter current of pure water (possibly permeate from the final reverse osmosis step). If the use of acid is wanted or necessary it is appropriate to use sulphuric acid at this stage. It is thus possible to achieve a higher final concentration of ammonia.

The scrubber condensator are preferably constructed from a polymer in order to allow the use of acids.

Ammonia Absorption Column (for Use With First and/or Second N-Stripping

A condensate scrubber is used in order to gain flexibility concerning addition of add. The column (Component number 21) is preferably constructed in two sections so that the fraction of ammonia not condensed in the first section is subsequently condensed in the second section. This takes place in a full counter current so that addition of water is limited as much as possible. Thereby a maximum ammonia concentration in the final condensate is reached (larger than 25%). The ammonia product can be pumped out with a separate pump or be taken out from a valve on the circulation pump. The absorption may be assisted by addition of sulfuric acid into the water counter current.

Sulphuric Acid Tank

The sulphuric acid tank is used for storing the sufuric acid used in the N-stripping process. (Component number 22).

NS Tank

The NS tank (Component number 23) is used for storing the stripped N.

Gas Store

It is preferred to establish a gas store (Component number 24) as a bufferstore for the feeding of e.g. a motorgenerator engine.

Rejectwater Tank

From the decanter installation the rejectwater is preferably pumped to the rejectwater tank (Component number 25).

The rejectwater tank is equipped with a submerged micro-filter with static operation. The micro-filter shall remove particles larger than 0.01-0.1 µm. A negative pressure of 0.2-0.6 bar shall be built up at the membrane. Hence the permeate is sucked through the membrane retaining the particles on the membrane surface. In order to prevent membrane fouling and scaling the coating of the membrane surfaces has to be removed by a periodic backwash procedure.

A micro-processor control device shall automatically control the extraction of permeate and the backwash procedure. The extraction shall be interrupted by periodic backwash e.g. for 35 seconds for every 300 seconds running time. The total flow shall be 2-6 m3 per h.

Aeration may be applied to assist the micro-filtration. Aeration impose shear stress on the membrane surface reducing scaling and fouling. It further aerates the rejectwater and stimulates aerobic decomposition of residual organic matter, nitrification and denitrification. Possible remaining odour, nitrate etc. is thus removed during the process of micro-filtration.

From this tank the permeate shall be used for:
Rinsing of the animal houses, canals, slats etc.
Further separation. Dissolved K shall be concentrated by means of reverse osmosis, the K-fraction being stored in a separate storage tank. Water for rinsing animals houses may also be taken form this permeate flow.
The K may also be concentrated through other means such as mechanical or steam compression. This depends on the specific choice for each specific plant and amount of excess heat available for steam compression.

The reject water tank containing the concentrate from the micro-filtration shall be emptied at regular intervals to remove the particle concentrate. This shall be added to either the K-fraction or the P-fraction from the decanter.

K Tank

The K tank (component number 26) serves the purpose of storing the potassium (K) concentrate.

Gas Cleaning

The biogas produced in the fermentors may contain trace amounts of hydrogen sulfide ($H_2S$) which are necessary to remove (Component number 27) before burning the biogas in a combined heat and power plant.

The gas shall be cleaned by employing the ability of certain aerobic bacteria to oxidise $H_2S$ into sulfate. The genus shall primarily be the genus *Thiobacillus* which is known form several terrestrial and marine environments. Other genus may also be used such as *Thimicrospira* and *Sulfolobus*.

A tank made of glass fiber packed with plastic tubes with a large surface area shall be rinsed with reject water to maintain the packing material moist. The biogas is diverted through the packed column and an air stream (of atmospheric air) is added to the biogas stream. The atmospheric air is added to provide an oxygen concentration of 0.2% in the gas stream, i.e. sufficient to oxidize the $H_2S$ and therefore not to produce an explosive mixture of biogas and oxygen. A ring side blower is used.

Combined Heat and Power Plant (CHP)

The main component in the CHP (Component number 28) can be e.g. a gas fired engine connected to a generator for production of electric power. The main priority for the CHP is to produce as much electric power as possible relatively to heat. The engine is preferably cooled by a water circuit (90° C.) and the heat is used in the plant process and to the heating of e.g. the animal houses.

The exhaust gas is used in a recuperator for steam production. The steam is used as heating source in the plant process, i.e. in the pressure sterilization unit and in the n-stripper unit II (priority one). Depending on the amount of steam it may also be used for concentrating the K in the rejectwater (seam evaporation).

Between the steam and heat circuit, there will be installed a heat exchanger, so it is possible to transfer heat from the steam system to the heat system.

In addition to the above mentioned genset there will be installed a steam boiler. This boiler will be used for heat production to start the process, and in addition be used as a backup for the genset.

If there is produced more steam than needed in the plant process, the rest production can be flashed of in a cooler.

To start the plant process (heating of fermentor tanks) etc., heat is provided by the oil fired boiler. As soon as gas production is achieved the oil burner will be switched to a gas burner. As soon as gas production is large enough to start the engine, the engine will take over the heat production.

Potassium Separation

At least two alternatives for separating potassium from the rejectwater are possible (Component number 29). At relatively high levels of biogasproduction the motorgenerator engine produces excess heat (steam at 160° C.) which can be used to concentrate the K. The distillate free of nutrients may be used for field irrigation or recycled through the whole plant.

At relatively low rates of biogasproduction a micro-filter can be used to filter particles larger than 0.01-0.1 ym from the reject water rendering the permeate suitable for treatment in a standard reverse osmosis filter. The K shall preferably be concentrated to a 10-20% solution.

The Second Aspect (BSE Prions)

In the second preferred aspect the invention may be applied to substantially reduce and/or eliminate BSE prions contained in manures, fodder, slaughterhouse waste, flesh and bone meal and the like. This is achieved by a combination of pre-treatment and digestion. This components as listed above are supplemented with a device for additional pre-treatment of the substrate containing BSE prions, e.g. a lime pressure cooker. The lime cooking can be used to hydrolyse a variety of organic substrates including material containing prions.

BSE prions are proteins resistant to protease attack. However, if treated with lime at temperatures of preferably 140-180° C., pressures at preferably 4-8 bar, and a pH of about 10-12 the prions are partly hydrolysed and thus rendered decomposable by microbial enzymes such as proteases, amidases etc. The microbes are present in the bioreactors and because the substrate is stripped for ammonia and thus low in total N versus total carbon the micro organisms are prone to produce additionally extracellular proteinases and proteases capable of hydrolysing the BSE prions. The high residence time also contributes to an efficient decomposition of BSE prions.

The Third Aspect (Concentration of N and P)

In a third preferred aspect, the invention may be applied to separate the main nutrients nitrogen (N) and phosphorus (P) from animal manures and refine the nutrients to fertilizer products of commercial or "organic" quality. This is achieved by combining the components of the first aspect with a decanter centrifuge.

The N and P are the main nutrients in the slurry which are often in excess in animal holdings. The N is stripped and collected as described in the first aspect leaving P in the remaining digested slurry. However, if subject to a decanter centrifuge, the P is removed from the slurry along with organic and inorganic solids.

The result being that preferably more than 90% of the N and P in the slurry are collected in separate fractions. The remaining reject water contains some potassium (K) and trace amounts of N and P. The reject water is thus suitable for land spreading at all times of the year.

It is possible to extract potassium (K) from the reject water by an additional coupled membrane aeration and filtration. Briefly, ceramic micro-filters are used as diffusers and filters at the same time. The filters are submerged in the reject water and operated with intermittent aeration and filtration periods. Aeration provides decomposition of the remaining organic matter and settling of inorganic flocks. The treated water is thus suitable for membrane filtration because fouling and scaling is prevented. Also the aeration through the same membranes (air back flushing) prevents the membranes from fouling and scaling.

The product produced is a concentrate (mainly containing K) and filtered water suitable for land spreading (a very limited area is required).

As under the first aspect the reject water may also be re-circulated through the animal houses.

The P fraction is suitable to further drying, which produces a granulate of commercial value. The N and K fractions are similarly of commercial value.

The third preferred aspect is in particular designed to concentrate the main nutrients N and P (and K) contained in slurry and other organic substrates to fertilizer products of commercial quality.

However, if decanter centrifuges are combined with the other elements of the GFE biogas and slurry separation system, in particular the N-stripping unit, it becomes of major interest to farmers. The combination of the N-stripping and decanter centrifuges means that the majority of the N and P content of the slurry is separated and collected into individual fractions. It is important to stress that the P when present in flocks is bound to be stripped by the decanter centrifuge.

They can be used and added to the fields according to the specific need of each nutrient It is also possible to re-circulate the reject water taken behind the decanter centrifuge through the animal houses. Cleaning of floors and slats in the sties are achieved as is additional advantages in terms of good indoor climate, reduced ammonia and other gas emissions, frequent flushing of slurry canals etc.

The reject water may contain a major fraction of the potassium (K), while a smaller part will be present in the P-fraction. This means that in the scenario where slurry is stripped for ammonia and separated for P the N and P can be stored and applied according to specific needs, while the reject water can be applied throughout the year as waste water.

It can be estimated that the need of spreading area is about ¼ of the area required for slurry application, the harmony area, and that this ¼ part shall run through the whole harmony area over a 4-year period.

Irrespectively of the possibility of treating the reject water further (see section) some farmers will undoubtedly be more than content with the N- and P-stripping with just one single reactor for digestion of the slurry. Even the P-stripping by the decanter centrifuge may be omitted because the N is concentrated leaving a dilute slurry without N which may also be spread onto land a any time of the year, except on frozen land.

It is very satisfying that parts of the total system can be offered to farmers while others may be content with any combination more suitable to their situations. In any case it is the N-stripping which make the use of decanter centrifuges interesting to practical farming.

The reject water from the complete process may be subjected to a final treatment depending on the market preferences.

Thus, the challenge is to treat the reject water to become suitable for membrane filtration and also larger volume reductions than the 50-60% mentioned. The challenge is also to use well known, cheap and robust technologies in a new context.

The solution is the following:

Aeration of slurry is well known and aeration with atmospheric air during 24 weeks produces an aerobic digestion.

Aeration achieves the following:

First, remaining ammonia is stripped and collected in an absorption column (possibly the same as the one used during pre-treatment) by a so-called low-temperature stripping of about 20° C. A wider liquid-gas ratio is required of about 1:2000 (Liao et al. 1995).

Secondly remaining organic matter and smell components are decomposed (Camarero et al. 1996; Burton et al 1998; Doyle and Noüe 1987; Garraway 1982; Ginnivan 1983; Bloun et al. 1988).

Thirdly possible remaining ammonia after stripping will be nitrified to nitrate (Argaman Y. 1984; Gönenc and Harremoës 1985).

This aeration shall be combined with filtration by employing new sewage waste technology, i.e., a micro-filtration principle combining aeration and filtration over ceramic filters (Bouhabila et al. 1998; Scott et al. 1998; Zaloum et al. 1996; Engelhardt et al. 1998). An energy efficient aeration and filtration is achieved in one operation. The aeration is further used for cleaning of the ceramic membranes by "air back flushing" (Visvanathan et al 1997; Silva et al 2000).

This leaves a water phase well suited to separation over standard osmosis membranes if necessary, because possible scaling and fouling problems are minimal. It is therefore hypothesized that a larger volume reduction can be achieved at substantial lower energy costs, although some energy is used for the aeration.

Even if membrane filtration is not used, aeration it self may be motivated by the final stripping of ammonia and by removal of the remaining smell components.

The Fourth Aspect (Renewable Energy)

The main devices of this preferred aspect are pre-treatment facilities consisting of a stripper tank and a lime cooker, and a flexible and multi step (minimum 3-step) process design of bioreactors.

In the fourth preferred aspect the invention may be applied to produce large amounts of biogas from a wide range of organic substrates including all types of animal manures, energy crops, crop residues and other organic wastes.

The pretreatment facilities of first and second preferred aspects allow the use of a variety of organic substrates while the multi-stage biogas plant allows a complete digestion of the substrate and thus a maximum energy yield.

N-rich and recalcitrant substrates such as poultry manure and deep litter is pretreated in the lime cooker. The cooked substrate is pre-digested in a mesopile reactor before the substrates enters the stripper tank and the subsequent reactors.

The pre-digestion ensures that the readily available organic matter is decomposed and the N released into solution as ammonia. The bulk of the N is thus is thus collected in the stripper tank and the recalcitrant organic substrate being decomposed in the subsequent reactors of the energy plant. Alternatively, depending on the quality of the substrate, it may enter directly into the stripper tank before digestion in the reactors. The result is that large amounts of biogas is being produced, i.e. typically 5 to 10 times more energy than contained in slurry.

The treatment in the GFE biogas and separation system further ensures that the nutrients are re-circulated to agricultural land. The energy crops are digested in a separate reactor and the digested biomass is diverted to the stripper tank. In this tank the fibres not decomposed during residence in the separate reactor will be hydrolysed and the ammonia will be collected in the N-fraction. The N contained in energy crops can then be re-circulated to land and used in the production of new energy crops. About 1-3 kg N per tonnes silage can be reused.

The organic material according to the invention is preferably stripped for ammonia which in particular at thermopile temperatures is inhibitory to the biogas process (Hansen et al. 1998; Krylova et al. 1997; Kayhanian 1994). The ammonia is stripped during the pretreatment, where the biomass is also being hydrolysed etc.

The process can preferably be split in a thermopile and a mesopile component (Dugba and Zhang 1999; Han et al. 1997; Gosh et al. 1985; Colleran et al. 1983). This gives rise to increased energy yields and working stability, among other thing because the biomass resides longer in the bioreactors which allows the methane bacteria time decompose the substrate. It should be noted that more energy for heating is required as is a larger total reactor volume.

In addition to this two-step principle the plant shall make use of yet another reactor to preliminary digestion of poultry manure and similar N-containing biomasses. Also the energy crops shall be digested in this reactor before further processing in the energy plant. During this first digestion the main fraction of the readily available organic matter is decomposed and the nitrogen released into solution in the form of ammonia. The nitrogen can now be stripped in the stripper tank and collected in the N-fraction.

Digested beets, maize, clover grass etc. contain about 1 kg N per tonnes wet weight and it is therefore important that this N is collected in the N-fraction. Poultry manure is even more N-rich and may also be digested in the pre-digester before further digestion in the main biogas plant.

The stripping and hydrolysis ensures that also the recalcitrant fibres are made available to digestion as described under the pre-treatment. The following digestion in the main biogas plant ensures a maximum gas yield.

The Fifth Aspect (Animal Welfare)

In a fifth preferred aspect the invention may be applied to ensure optimal animal welfare and health when stabled in the animal houses while at the same time reducing emissions of dust and gasses such as ammonia. This is achieved by flushing or re-circulating reject water through the animal houses with the purpose of cleaning and rinsing sties, floors, slats, manure canals etc. This reduces the emitting surfaces where odour, ammonia and dust may be released to the in-door air.

The system further allows the use of straw without increasing the emissions of dust and ammonia. The straw is a substantial welfare component, in particular for pigs but also for other animals. It provides the animals with digging and occupational material and structural fodder.

The reject water taken after the decanter centrifuge treatment (the third aspect) or possibly behind the first digestion (the first aspect) is well suited as a means to flush the animal housings. The flushing removes the straw and manure mixtures from the slats.

In further preferred aspects any combination of the core invention with the other aspects mentioned may be preferred. The first aspect is preferably included in all combinations.

Accordingly, it will be clear from the above descriptions of preferred aspects and embodiments of the present invention that there is provided herein:

A method for improved biogas production, said method comprising the steps of
i) stripping N including ammonia from organic materials including manures and slurries thereof, and optionally hydrolysing the organic material,
ii) diverting the thus obtained organic material to a biogas fermentor, and
iii) obtaining biogas from the fermentation of the organic material.

The above method may further comprise the step of separating the solids resulting from the biogas fermentation in a separation step involving a decanter centrifuge. Separate fractions of P and/or K, preferably in granulated form, are obtained from this separation.

The above method in another embodiment comprises the further step of recirculating the liquids resulting from the biogas fermentation to stables or animal houses, optionally after a further purification step.

In another preferred embodiment, the step of N including ammonia stripping preferably occurs simultaneously with, or sequentially with, in any order, a step involving a thermal hydrolysis step and/or an alkali hydrolysis step, wherein any one or both steps take place at an increased temperature and/or an increased pressure as described herein above.

The above preferred embodiments thus in one embodiment solve the problems associated with environmental contamination by undesirable microbial organisms, including *Salmonella Typhimurium* DT104, and/or prions associated with BSE that are present in organic materials including manures and slurries thereof.

In another embodiment, the above described preferred embodiments solve the problems associated with an attaining a sufficiently high hygienic standard in a stable or an animal house. This is achieved by reducing and/or eliminating undesirable microbial organisms and/or prions associated with BSE that are present in organic materials including manures and slurries thereof.

In yet another embodiment, the above described preferred embodiments solve the problems associated with an excessive use of expensive water resources in a stable or an animal house. This problem is solved by re-using reject water obtained from the decanter centrifuge separation step used for separating solids and liquids resulting i.e. from either pre-treatment of organic material and/or N stripping including ammonia stripping and/or anaerobic fermentation leading to biogas formation. At the same time, it is possible to reduce and/or eliminate the occurrence of microbial microorganisms in the reject water by further purification steps.

The present invention also provides cheep fertilisers of commercially acceptable standards. This is achieved by N-stripping including ammonia stripping and separation of P-containing granulates and K-containing granulates by means of decanter centrifugation following pretreatment, preferably including thermal and alkali hydrolysis.

In another aspect of the present invention there is provided a method for reducing the number of viable microbial organisms and/or BSE prions present in an organic material, said method comprising the steps of
i) providing an organic material comprising solid and/or liquid parts,
ii) reducing, in said organic material, the number of viable microbial organisms and/or BSE prions by subjecting the organic material to
a) a lime pressure cooking step, and/or
b) a step wherein the organic material is heated at a predetermined temperature and/or subjected to a predetermined pressure and/or subjected to addition of base or acid, and/or
c) a step resulting in at least partial hydrolysis of the organic material,
wherein said processing steps a), b) and c) can occur simultaneously, or sequentially in any order, and
iii) obtaining a processed organic material comprising at least a reduced number of viable microbial organisms and/or BSE prions.

A wide variety of microbial organisms can be eliminated by the methods of the invention, including microbial organisms selected from animal microbial organisms, infectious microbial organisms, and parasitic pathogen microbial organisms, including any combination thereof. Examples include, but is not limited to, bacteria such as *Campylobacter, Salmonella, Yersinia, Ascaris*, similar microbial and parasitic organisms, as well as virus, viroids and the like.

The lime cooking step may also serve to sterilize the organic material in which case no viable microbial organisms survive this step of processing. The lime preferably comprises or essentially consists of CaO or $Ca(OH)_2$.

Preferably, any BSE prions or other prions present in the organic material are also destroyed or eliminated by the sterilization process. When there is a reduction of microbial organisms and/or prions following any one of the above-mentioned steps, the reduction be e.g. a 90% reduction, an 80% reduction, a 70% reduction, a 60% reduction, or a reduction of preferably at least 50%.

It is preferred in one embodiment to improve the production of biogas by lime pressure cooking the organic material before the organic material is subjected to a N stripping step. However, the lime pressure cooked organic material can also be fermented prior to being subjected to a N stripping step.

When the organic material is of plant origin, it can preferably be ensued before being diverting to N stripping. The ensued organic material of plant origin can also be fermented prior to N stripping. Organic material to be ensilaged preferably comprises annual fodder crops such as beets, maize, clover grass, and wherein optionally the top of the plants is included.

Lime pressure cooking of the organic material is preferably performed at a temperature of from about 100° C. to about 250° C., under a pressure of 2-20 bar, with addition of lime sufficient to reach a pH value of from about 9 to about 12, and with an operation time of from at least one 1 minute to preferably about less than 60 minutes.

The amount of added lime including CaO is preferably from about 2 to about 80 g per kg dry matter, such as from about 5 to about 80 g per kg dry matter, such as from about 5 to about 60 g per kg dry matter, such as from about 10 to about 80 g per kg dry matter, such as from about 15 to about 80 g per kg dry matter, such as from about 20 to about 80 g per kg dry matter, such as from about 40 to about 80 g per kg dry matter, such as from about 50 to about 80 g per kg dry matter, such as from about 60 to about 80 g per kg dry matter.

An example of operating conditions of the lime pressure cooker is a temperature in the interval of about 120° C. to about 220° C., a pressure from about 2 bar to preferably about less than 18 bar, and an operation time of from at least 1 minute to preferably less than 30 minutes.

Another example of working conditions includes a temperature in the interval of from about 180° C. to about 200° C., wherein the pressure is from about 10 bar to preferably less than 16 bar, wherein the pH level is from about 10 to about 12, and wherein the operation time is from about 5 minutes to about 10 minutes.

The above method can be following by a number of additional steps. In one embodiment, there is provided the further steps of diverting the processed organic material to a biogas fermenter, fermenting the processed organic material and obtaining a biogas. Another further step relates to supplementing an external environment, including an agricultural field, with the processed organic material. The supplementation of the external environment, including an agricultural field, can also be performed by using the residual material resulting from the fermentation of the processed organic material.

Another further step is that of stripping nitrogen (N), including ammonia, from said organic material prior to diversion to a biogas fermentor of the organic material. This results in an increased and stable biogas production. This also allows the use of N-rich biomasses to be stripped and subsequently digested in the fermentors. Biogas is produced from the fermentation of the organic material freed from at least part of the N, including ammonia.

The stripped nitrogen (N) including ammonia is preferably absorbed in a column before optionally being stored in a tank. When being absorbed in a column, the stripped nitrogen (N) including ammonia is preferably absorbed in a column comprising water or an acidic solution, preferably sulphuric acid, before optionally being stored in a tank.

In one presently preferred embodiment there is provided a method comprising the steps of
i) eliminating, inactivating and/or reducing in said organic material the number of viable microbial organisms and/or BSE prions by subjecting the organic material to
 a) a lime pressure cooking step, and/or
 b) a step wherein the organic material is heated at a predetermined temperature and/or subjected to a predetermined pressure and/or subjected to addition of base or acid, and/or
 c) a step resulting in at least partial hydrolysis of the organic material,
 wherein said processing steps a), b) and c) can occur simultaneously, or sequentially in any order,
ii) stripping N, including ammonia, from said processed organic material,
iii) diverting the N stripped organic material to a biogas fermenter,
iv) fermenting the N stripped organic material, and
v) obtaining biogas and a fermented organic material at least having a reduced number of viable microbial organisms and/or BSE prions.

It is much preferred that essentially no BSE prions are present in the organic material resulting from the fermentation.

The step of stripping nitrogen (N), including ammonia, is preferably performed by initially adding an amount of lime to the organic material sufficient to increase the pH value to above 9 at a temperature of preferably above 40° C., such as a pH value of above 10 at a temperature of preferably above 40° C., for example a pH value of above 11 at a temperature of preferably above 40° C., such as a pH value of about 12 at a temperature of preferably above 40° C.

In preferred embodiments, the temperature is preferably above 50° C., such as above 55° C., for example above 60° C.

The operation time is in one embodiment from 2 to 15 days, such as from 4 to 10 days, for example from 6 to 8 days. An example of one set of process parameters is a pH level of from 8-12, a temperature of from 70° C.-80° C., a liquid to gas ratio of less than 1:400, and an operation time of about 7 days. The alkaline conditions can be generated by adding any base. However, the pH is preferably increased by adding CaO or Ca(OH)$_2$.

The organic material can comprise solid and/or liquid parts such as e.g. manures and slurries thereof, crop residues, silage crops, animal carcasses or fractions hereoff, slaughterhouse waste, meat and bone meal, including any combination thereof. In one embodiment, the organic material comprises a maximum of 50% solid parts, for example a maximum of 40% solid parts; such as a maximum of 30% solid parts, for example a maximum of 20% solid parts. The organic material can also be in a liquid state and comprise a maximum of 10% solid parts.

The organic material can further comprise straw, fibres or sawdust, and in one embodiment the organic material has a high content of fibres, preferably more than 10% (w/w). The organic material can also have a high content of complex carbohydrates comprising cellulose, and/or hemicelluloses and/or lignin, such as preferably more than 10% (w/w). Lime pressure cooking cellulose containing organic material results in a disintegration of cellulose into small organic acids such as formic acid, acetic acid, lactic acid, and the like.

The organic material can also comprise deep litter or manure from animals, especially from cattle, pigs and poultry holdings. Additionally, animal organic material can be used, such as e.g. animal carcasses or fractions hereof, slaugtherhouse waste, meat and bone meal, blood plasma or any such produce originating from animals, risk- and no-risk material with respect to the potential presence of BSE-prions or other prions.

In one embodiment the organic material comprises or essentially consists of solid parts of less than 10 cm in length, such as solid parts of less than 5 cm in length, for example solid parts of less than 1 cm in length.

The organic material can preferably be macerated before being treated in the lime pressure cooker, preferably by using a screw conveyor equipped with a macerator, preferably one made of rust and acid proof steel. The conveyor conveys the organic material into the lime cooker where the organic material is preferably heated by steam injection, or by steam in a cape around the lime cooker, or any combination thereof.

The organic material can also comprise proteins or similar organic molecules comprising elements, including amino acids and combinations thereof, constituting the BSE prions or other prions, and wherein said BSE prions or other prions are eliminated or destructed directly or rendered available for destruction by lime pressure cooking and/or subsequent fermentation, including anaerobic fermentation. The organic material of animal origin preferably has a high amount of nitrogen (N), preferably more than 10%.

The organic material in the form of a liquid slurry can be obtained by the addition of water and/or water containing a low concentration of organic material, preferably less than 10% solid parts. The added water can be recycled water, water containing a low concentration of organic material obtained from the silage plant, and/or water collected following cleaning of stables and/or cleaning of animals, and/or water obtained from the fermentation before the N stripping process, and/or water obtained from one or more biogas producing plants, and/or water obtained during concentration of P fertilisers, and/or water obtained during concentration of K fertilisers, and/or collected rain water.

It is in one embodiment particularly preferred that the water is reject water obtained from a biogas producing plant, or reject water obtained during concentration of P fertilisers, or water obtained during concentration of K fertilisers, or collected rain water.

It is preferred that any or most of the urea and/or uric acid present in the organic material is converted into to ammonia, wherein the ammonia is optionally collected following absorption to a column as described elsewhere.

Additional steps besides lime pressure cooking is mesophilic and/or thermophilic fermentation. Accordingly, the organic material which has been treated in the lime pressure cooker can subsequently be diverted into a plant for mesophilic and/or thermophilic fermentation before or after the organic material is subjected to N stripping.

Each fermentation is performed by a bacterial population capable of mesophilic or thermophilic fermentation, respectively. The fermentation is in one embodiment an anaerobic fermentation.

The fermentation is preferably performed at a temperature of from about 15° C. to preferably less than about 65° C., such as at a temperature of from about 25° C. to preferably less than about 55° C., for example at a temperature of from about 35° C. to preferably less than about 45° C.

The fermentation is preferably performed for a period of time from about 5 to preferably less than 15 days, such as for a period of time from about 7 to preferably less than 10 days.

There is in one embodiment provided a method, wherein the biogas production is performed in one or more plants by a microbial organism, preferably a population of bacteria, and involves an anaerobic fermentation of the organic material. The bacteria preferably produce mainly methane and a smaller fraction of carbon dioxide when fermenting the organic material. The biogas production can be performed in one or more plants, preferably by bacterial anaerobic fermentation of the organic material.

In one embodiment, the biogas production is performed in two plants by anaerobic bacterial fermentation of the organic material, initially by fermentation with thermophilic bacteria in a first plant, followed by diverting the thermophilicly fermented organic material to a second plant, wherein fermentation with mesophilic bacteria takes place.

The thermophilic reaction conditions preferably include a reaction temperature ranging from 45° C. to 75° C., such as a reaction temperature ranging from 55° C. to 60° C.

The mesophilic reaction conditions preferably include a reaction temperature ranging from 20° C. to 45° C., such as a reaction temperature ranging from 30° C. to 35° C. The thermophilic reaction as well as the mesophilic reaction is preferably performed for about 5 to 15 days, such as for about 7 to 10 days.

Any potential foam formation can be reduced and/or eliminated by the addition of polymers, and/or plant oils, and/or one or more salts, preferably plant oil in the form of rape oil. The salts preferably comprise or essentially consist of CaO and/or $Ca(OH)_2$.

A desirable flocculation of substances and particles during biogas production is preferably achieved by the addition of calcium-ions capable of forming calcium-bridges between organic and inorganic substances in solution or suspension, wherein said calcium-bridges resulting in the formation of 'flocks' of particles. The addition of calcium-ions further results in the precipitation of orthophosphates, including dissolved ($PO_4^{3-}$), which is preferably precipitated as calcium phosphate $Ca_3(PO_4)_2$, wherein the precipitated calcium phosphate preferably remains suspended in a slurry.

The obtained biogas can be diverted to a gas engine capable of producing heat and/or electricity. The heat can be used to heat the lime pressure cooker and/or the fermentation plant and/or the N stripper reactor and/or the one or more biogas plant(s) and/or the animal house(s) and/or a human residence and/or heating water to be used in a household or human residence. The electricity can be diverted and sold to a commercial net for distributing electricity. In one preferred embodiment, the remaining N stripped, sterilised and fermented organic material is spread on agricultural fields.

In addition to i) reducing and/or eliminating undesirable microbial organisms, ii) improving the production of biogas, and iii) providing a highly usable N stripped, sterilised and fermented organic material, the invention in another aspect pertains to a method for producing N comprising fertilisers from organic materials comprising a N source, said production comprising the steps of i) collecting N including ammonia stripped from the organic material in an N stripping step, ii) absorbing said N including ammonia in water or an acidic solution preferably comprising sulphuric acid, and iii) obtaining N-fertiliser which can be spread on agricultural land.

The invention in yet another aspect provides a method for producing phosphor (P) comprising fertilisers from organic materials comprising a P source, said production comprising the steps of i) diverting slurry from a biogas fermenter to a separator, ii) separating the fermented organic material as well as inorganic material into a solid and a mainly liquid fraction, iii) obtaining a mainly solid fraction comprising a part of the P, preferably in the form of calcium phosphate $Ca_3(PO_4)_2$, and organic phosphates suspended in the slurry, wherein said solid fraction is capable of being used as a P fertiliser capable of being spread on agricultural land when appropriate.

The separator for separating the fermented organic material as well as inorganic material into a solid and a mainly liquid fraction is preferably a decanter centrifuge. The mainly solid fraction comprising P can optionally be dried to produce a granulate comprising a P fertiliser, e.g. by allowing the P-fraction to compost in a mile store under an air permeable sheet or cover.

The reject water obtained from the biogas production and the separation from solid components can preferably be re-used in the fermentation of silage and/or in the lime pressure cooking process and/or in the N stripping process and/or in the biogas plant and/or in cleaning of the stable and/or is spread on land and/or is lead to a conventional sewage treatment plant.

Accordingly, the method in another aspect provides for the production of substantially clean reject water, said production comprising the steps of i) obtaining from the separator, preferably a decanter centrifuge, a liquid fraction comprising reject water having only a very limited content of N and P, preferably less than 5% (w/v), such as less than 1% (w/v), for example less than 0.1% (w/v), such as less than 0.01% (w/v), and essentially no sources capable of spreading zoonoses, veterinary vira, infectious bacteria, parasites or other infectious agents, including BSE prions and other prions. For some embodiments it is acceptable if the reject water contains less than 10% of the N and P originally obtained in the slurry.

In another aspect of the present invention there is provided a method for producing potassium (K) comprising fertilisers from organic materials comprising a K source, said production comprising i) diverting the liquid fraction from the first separation step (used in the separation of P containing organic materials as described herein above) to a second separation step, ii) separating the remaining organic and inorganic composition from the liquid, iii) obtaining a solid fraction comprising K, wherein said solid fraction is capable of being used as a K fertiliser capable of being spread on agricultural land when appropriate.

The second separation step preferably comprises subjecting the K comprising fraction through a ceramic micro filter operating with an intermittent aeration and filtration of the reject water, wherein preferably said aeration provides decomposition of the remaining organic material and settling of inorganic flocks.

In another aspect there is provided a method for producing clean reject water, wherein the obtained reject water is treated in an aerobic treatment system capable of eliminating and/or reducing the content of N and P within the water and preferably also decomposing the remaining organic material and smell components, obtaining reject water essentially free from N and P, wherein said reject water is preferably capable of being spread on agricultural land when appropriate, or re-circulated through an animal houses.

The above-mentioned aeration can be performed with atmospheric air during 2-4 weeks at a temperature of about 20° C. and a liquid-gas ratio of about 1:2000. Any eliminated N can be collected and diverted to the absorption column described herein elsewhere.

By being able to clean animal houses with the reject water treated in this way, the invention also provides in yet another aspect a method for improving the hygiene in an animal house or a stable for animals, said improvement consisting in cleaning the stable with the obtained reject water. The cleaning involves cleaning and rinsing e.g. sties, floors, slats, manure canals, ceilings, ventilation canals, scrubbing exhaust air, etc., as well as reducing the emitting surfaces where odour, ammonia and dust may be released into the environment of the predetermined location including the stable.

The cleaning of the stables is in one embodiment preferably performed with reject water obtained following fermentation of energy crops or obtained following the fermentation to produce biogas separation of solids and liquids or reject water obtained from a later process in the system.

It is also possible according to this aspect of the invention to improve animal welfare in a stable by utilising straw in the stable as it provides the animals with digging and occupational material and structural fodder. It is preferred in one embodiment to divert the straw comprising organic material from the stable to the lime pressure cooker and hydrolyse the organic material before further processing. Another overall objective of the improvement of animal welfare in a stable resides in the possibility of being able to spray the animals in order to reduce the number of microbial organisms as well as dust in the furs of the animals and simultaneously reduce the temperature of the animals.

In this way, there is provided a method integrating anaerobic fermentation of animal manures, energy crops and similar organic substrates, as well as refinement of nutrients held in the digested biomass to fertilizers of commercial quality, in combination with obtaining clean reject water.

The integrated method described herein above requires a system of components, or a selection of such components, as described herein in more detail elsewhere.

In one aspect, the system comprises
  i) a first device, preferably animal houses or stables for holding and/or breeding animals, preferably farm animals including cows, pigs, cattle, horses, goats, sheep and/or poultry, and the like, and/or
  ii) a second device, preferably at least one pre-treatment plant for pretreatment of organic material, said organic material preferably comprises animal manure and/or animal slurry and/or plant parts, wherein said plant parts preferably comprise one or more of straw, crops, crop residues, silage, energy crops, and optionally animal carcasses or fractions hereof, slaugtherhouse waste, meat and bone meal, blood plasma or any such produce originating from animals, risk- and no-risk material with respect to the potential presence of BSE-prions or other prions, and/or
  iii) a third device, preferably an energy plant generating an improved amount of energy from a biomass comprising organic material,
  in which the first device comprises
  a) a system for cleaning one or more of floors, slats, sties, manure canals, slurry canals, animals, and ventilation canals of an animal house or a stable, said cleaning involving the use of cleaning water, and/or
  b) a system to transport the cleaning water, optionally in the form of a slurry comprising cleaning water and organic material, from the animal house or stable to the second device,
  in which the second device comprises
  a) a first pre-treatment tank, preferably a stripper tank for i) stripping N (nitrogen), including ammonia, from the slurry diverted from the first device to the second device, or ii) stripping N, including ammonia, from organic material diverted from an additional pretreatment tank of the second devise, wherein the first pre-treatment tank can optionally also be used for hydrolysing the organic material, and/or
  b) a second pre-treatment tank, preferably a lime pressure cooker for hydrolysing slurry comprising organic material diverted from the first device to the second device, wherein said hydrolysis results in eliminating, inactivating and/or reducing in number any viable microbial organisms and/or pathogenic substances present in the slurry, or a part thereof, and/or c) at least one tank, preferably a silage tank for generating ensued plant material comprising at least one or more of corn/maize, energy crops, beets, and crop residues, and/or d) at least one second tank, preferably a pretreatment fermenting tank to ferment silage and/or lime pressure cooked organic material, in which the fermentation conditions are selected from mesophilic fermentation conditions and/or thermophilic fermentation conditions, in which the third device comprises a) at least one biogas fermenter to which slurry and/or organic material can be diverted from the second device for fermenting the organic material under either mesophilic fermentation conditions and/or thermophilic fermentation, said fermentation resulting in the production of biogas comprising mainly methane and/or b) at least one tank for collection of biogas, wherein the tank is optionally connected to an outlet for distribution of biogas, or connected to a gas engine, and/or c) at least one first separator, preferably a decanter centrifuge in which the fermented material from the at least one biogas fermenter is separated into an essentially liquid fraction in the form of reject water, and an essentially solid fraction, wherein said solid fraction comprises solid phosphor (P) comprising organic and inorganic material, and/or d) at least one second separator, preferably a ceramic micro-filter in which the reject water from the at least one first separator is further processed, preferably by aeration and filtration, wherein said processing results in removing at least some and preferably a majority of one or more of odour components, nitrogen (N) compounds and potassium (K) compounds, wherein said separation further results in the generation of reject water comprising a reduced amount of any one or more of odour components, nitrogen (N) compounds and potassium (K) compounds as compared to the amount prior to separation.

The system preferably comprises pipe lines constituting a closed system preventing or leading to a reduction in emissions of any one or more of dust, microbial organisms, ammonia, air, liquid or any other constituent within the system.

Liquid fractions or reject water from one or more of the at least one silage tank, the at least one pre-treatment fermenting tank, the at least one biogas fermentor, the at least one first separator and the at least one second separator is preferably re-used for cleaning of the animal house or the stable.

The liquid fractions or reject water from any one or more of the at least one silage tank, the at least one pretreatment fermenting tank, the at least one biogas fermentor, the at least one first separator and the at least one second separator is preferably re-used in any step of the slurry separation and biogas production system to maintain the organic material in a proper fluid condition.

The system makes it possible to add lime, including CaO and/or $Ca(OH)_2$, to the organic material before said organic material enters the stripper tank for stripping N including ammonia, preferably by adding an amount of lime sufficient to generate a pH value of from about 10 to about 12, optionally in combination with a heating step and an aeration of the slurry including the organic material.

The organic material preferably remains in the stripper tank of the system for a period of 5 to 10 days, such as 7 days. The temperature inside the stripper tank is preferably between 60° C. and 80° C. An amount of from about 30 and 60 gram $Ca(OH)_2$ per kg dry matter in the organic material is preferably added to the organic material in the stripper tank or before said organic material enters the stripper tank.

The system facilitates collection of stripped N including ammonia from the stripper tank and diversion of said stripped N to a column in which N including ammonia is absorbed in water or an acid solution preferably comprising sulphuric acid, and optionally also storing the absorbed ammonia in a tank. The N absorbed in water or an acid solution in this way is preferably used as a fertiliser.

The lime pressure cooker of the system is preferably an apparatus which is initially capable of cutting the organic material into segments and subsequently capable of diverting the segmented organic material to a chamber wherein said segmented organic material is heated and simultaneously exposed to a high pressure due to the elevated temperature. The organic material to be treated in the lime pressure cooker is added an amount of lime, including CaO and/or $Ca(OH)_2$, prior to or after entry into the lime pressure cooker.

Preferably CaO is added to the lime pressure cooker in an amount of from 5-10 g per kg dry matter in the organic material. The system operates at a temperature of between 100° C. and 220° C., such as e.g. 180° C. to 200° C. The temperature is aligned according to the organic material to be treated, a higher temperature is chosen the higher the content of cellulose, hemicellulose and lignin is in the organic material, or a higher temperature is chosen according to the risk of infectious microbial organism or pathogenic compounds including BSE prions in the organic material.

The pressure is between preferably between from 2 to preferably less than 16 bar, such as from 4 to preferably less than 16 bar, for example from 6 to preferably less than 16 bar, such as from 10 to preferably less than 16 bar. The system operates at the elevated temperature for about 5 to 10 minutes, but longer treatment times can also be used.

N including ammonia stripped in the lime pressure cooker is preferably collected and diverted to a column and absorbed as described herein elsewhere.

The system in one embodiment facilitates diversion of silage such as e.g. maize, energy crops, beets, and/or crop residues, to a mesophilic or thermophilic fermentation tank, before the material is further diverted to the stripper tank.

The system can also facilitate diversion of lime pressure cooked organic material to a mesophilic or thermophilic fermentation tank, before the material is diverted to the stripper tank.

The system also facilitates the optimization of the fermentation of the organic material and the production of biogas by providing a pre-treatment plant comprising facilities for stripping N including ammonia and/or performing alkaline hydrolysis under predetermined process parameters, including pH level, temperature, aeration, duration, foam inhibition and flocculation of suspended material.

The system in another embodiment ensures optimised conditions for the population of microbial organisms contained in the biogas producing fermenters. This is achieved by e.g. diverting sterilised or sanitised slurry from the stripper tank to at least a first biogas fermenter, wherein said sterilised or sanitised slurry do not inhibit or harm the population of biogas producing microbial organism in the fermenter. In particular, organic material from which N including ammonia is stripped, can be diverted to a biogas reactor in which the fermentation conditions supports a mesophilic fermentation. Once the organic material has been subjected to a mesophilic fermentation, the organic material is preferably diverted to another biogas reactor of the system, in which the fermentation conditions are capable of supporting a thermophilic fermentation.

The thermophilic reaction conditions include a reaction temperature ranging from about 45° C. to 75° C., such as a reaction temperature ranging from about 55° C. to 60° C. The mesophilic reaction conditions include a reaction temperature ranging from about 20° C. to 45° C., including a reaction temperature ranging from about 30° C. to 35° C.

The system allows for both the thermophilic reaction and the mesophilic reaction to occur for about or at least 5-15 days, such as for about or at least 7-10 days, preferably at least 7 days.

The system comprises devices capable of preventing foam formation, wherein said devices are capable of adding e.g. polymers, and/or plant oils, including rape oil, and/or different salts, including salts comprising CaO and/or Ca(OH)$_2$.

The system makes it possible to reuse at least part of the fermented organic material from the biogas reactors in that same reactor, wherein said fermented organic material functions as an inoculum of the population of microbial organism performing the fermentation.

The system makes it possible in one embodiment to divert a slurry including a liquid comprising solid parts, to a first separator for separating the solid materials including a limited fraction of the liquid from the main part of the liquid fraction. Said mainly solid fraction comprises organic and inorganic material including P (phosphor) and compounds hereof. Said mainly solid fraction can be further dried and comprises a fertiliser. The first separator of the system is preferably a decanter centrifuge.

The system also allows reject water from the first separator to be treated in a second separator, said second separator comprising a ceramic micro-filters in which the reject water from the first separator is further processed by aeration and filtration, optionally removing any residual odour components, any residual nitrogen compounds and/or any components containing K (potassium), leaving an essentially clean reject water comprising essentially none of said residual components.

The system makes it possible to divert the reject water from the thermophilic biogas reactor or from the first and/or second separator to an agricultural field, to a waste water treatment plant, or a purifying plant, or a biological treatment plant for further purification if required.

The system or the methods of the present invention can be used to:

eliminate or decline the emission to the environment of dust, microbial organisms, ammonia, contaminated air, liquid or any other constitution within the system, especially from animal houses.

improve the utilisation of the energy contained in a biomass including organic material.

improve the production of biogas comprising methane gas and methane-bearing gas. Said gas may be stored in a tank locally and/or can be diverted to a commercial net of distributing gas.

obtain separate fractions of N (nitrogen), P (phosphor) and potentially K (potassium) from organic materials. Said fractions are of commercial value and can be utilised as fertilisers to fertilise agricultural and horticultural crops.

obtain an improved animal welfare and improved hygiene in animal stables and in accordance to output from said animal stables. Said output comprising manure, slurry and animals to be slaughtered. The clean animals reduces the risk of infection of meat when the animals are slaughtered.

obtain a procedure for rendering animal carcasses or fractions hereof, meat and bone meal or any other produce from animals available for disposing off to agricultural land in the form of refined fertilizers and thus to benefit from micro- and macro-nutrients in the animal produce in the agricultural or horticultural plant production.

The invention claimed is:

1. A method for producing a processed organic material characterized by a reduced number of viable microbial organisms, infectious agents, and/or prions relative to that present in an organic material from which it is derived, and for producing biogas from at least some of said processed organic material, said method comprising the steps of
   i. providing an organic material comprising solid parts or solid and liquid parts, wherein said organic material comprises viable microbial organisms, infectious agents, prions, or combinations thereof, and wherein said solid parts comprise a plant material, an animal material, or a combination thereof, said plant material comprising cellulose, hemicellulose, lignin, or combinations thereof and said animal material comprising slaughterhouse waste, meat, bone meal, or combinations thereof;
   ii. subjecting said organic material, to the processing steps of:
       a. lime pressure cooking under pressure at a temperature of 120° C. to 250° C. and a pH-value of above 9 obtained at least in part by adding lime prior to or during said lime pressure cooking, said lime pressure cooking resulting in hydrolysis of the organic material, wherein when said organic material comprises plant material said lime pressure cooking further comprises hydrolysis of the cellulose, hemicellulose, and/or lignin of said solid parts, wherein the lime is Ca(OH)2 and/or CaO; and
       b. stripping ammonia from said lime pressure cooked organic material, thereby obtaining a processed organic material comprising a reduced number of viable microbial organisms, infectious agents and/or prions, and further comprising hydrolysed solid parts of the provided organic material of step (i);
   iii. directing at least some of the processed organic material comprising hydrolysed solid parts of organic material to one or more biogas fermenters;
   iv. fermenting the processed organic material in the one or more biogas fermenters, thereby producing a biogas; and
   v. obtaining the biogas from the biogas fermenter.

2. The method of claim 1, wherein said microbial organisms are veterinary microbial and zoonotic pathogens.

3. The method of claim 1, wherein said microbial organisms are selected from infectious microbial organisms and parasitic pathogen microbial organisms.

4. The method of claim 1, wherein said organic material comprising said solid parts or said solid and liquid parts is selected from the group consisting of a crop residue, a silage crop, an animal carcass or a portion thereof, a manure or slurry thereof, said slaughterhouse waste, said meat, said bone meal, and combinations thereof.

5. The method of claim 1, further comprising (ii) (a') fermenting at least some of the lime pressure cooked organic material prior to the stripping ammonia step (ii) (b).

6. The method of claim 1, said organic material of step (i) comprising organic material of plant origin, and said method further comprising ensiling the organic material of plant origin before the stripping ammonia step (ii) (b).

7. The method of claim 6, further comprising fermenting the ensiled organic material prior to the stripping ammonia step (ii) (b).

8. The method of claim 1, wherein the step (ii) (b) of stripping ammonia is performed at a pH value above 9 and a temperature above 40° C.

9. The method of claim 8, wherein the pH value in the stripping ammonia step (ii) (b) is above 10.

10. The method of claim 8, wherein the pH value in the stripping ammonia step (ii) (b) is above 11.

11. The method of claim 8, wherein the stripping ammonia temperature is above 50° C.

12. The method of claim 8, wherein the stripping ammonia temperature is above 60° C.

13. The method of claim 8, wherein the operation time of the stripping ammonia step (ii) (b) is from 2 to 15 days.

14. The method of claim 8, wherein the operation time of the stripping ammonia step (ii) (b) is from 4 to 10 days.

15. The method of claim 8, wherein the operation time of the stripping ammonia step (ii) (b) is from 6 to 8 days.

16. The method of claim 8, wherein the organic material of step (i) comprises a maximum of 500 (w/v) solid parts.

17. The method of claim 8, wherein the organic material of step (i) comprises a maximum of 30% (w/v) solid parts.

18. The method of claim 8, wherein the organic material of step (i) comprises a maximum of 10% (w/v) solid parts.

19. The method of claim 8, further comprising absorbing the stripped ammonia in a column and then storing the column-absorbed, stripped ammonia in a tank.

20. The method of claim 19, wherein the column comprises water or an acidic solution.

21. The method of claim 20, wherein the acidic solution is sulphuric acid.

22. The method of claim 1, wherein in step (ii) (a) the lime pressure cooking of the organic material is performed at a temperature of from 120° C. to 220° C., at a pressure of 2 to 20 bar, with addition of lime sufficient to reach a pH value of from above 9 up to 12, and with an operation time of the step of lime pressure cooking of from at least 1 minute to less than 60 minutes.

23. The method of claim 22, wherein, in the lime pressure cooking step (ii) (a), the temperature is in the interval of 180° C. to 200° C., wherein the pressure is from 10 bar to less than 16 bar, wherein the pH value is from 10 to 12, and wherein the operation time of the step of lime pressure cooking is from 5 minutes to 10 minutes.

24. The method of claim 22, wherein the organic material further comprises deep litter or manure from cattle, pigs and poultry.

25. The method of claim 22, wherein the organic material further comprises proteins constituting bovine spongiform encephalopathy (BSE) prions or other prions, wherein said BSE prions or other prions are substantially reduced or eliminated in the lime pressure cooking step.

26. The method of claim 22, wherein said solid parts of the provided organic material of (i) comprise said plant material in a form selected from the group consisting of straw, fibres or sawdust.

27. The method of claim 22, wherein the provided organic material has a content of fibres of more than 10% (w/w).

28. The method of claim 22, wherein the provided organic material has a content of complex carbohydrates comprising said cellulose and/or said hemicellulose and/or said lignin, of more than 101 (w/w).

29. The method of claim 22, wherein the lime pressure cooking step (ii) (a) comprises adding the CaO in an amount of from 2 to 80 g per kg dry matter of the provided organic material of (i).

30. The method of claim 22, wherein the lime pressure cooking step (ii) (a) comprises adding the CaO in an amount of from 5 to 60 g per kg dry matter of the provided organic material of (i).

31. The method of claim 22, further comprising macerating the provided organic material before the lime pressure cooking step (ii) (a).

32. The method of claim 31, further comprising conveying the macerated organic material into a lime pressure cooker, wherein the macerating and conveying of the provided organic material comprises macerating and conveying by means of a screw conveyor equipped with macerator; and in step (ii)(a) providing said lime pressure cooking by heating the conveyed organic material, wherein the heating comprises providing steam injection into the lime pressure cooker, providing steam in a cape around the lime pressure cooker, or by a combination thereof.

33. The method of claim 22 comprising the further step (ii) (a') of fermenting, under mesophilic and/or thermophilic fermentation conditions, at least some of the organic material treated in the lime pressure cooking step (ii) (a) before subjecting said organic material to stripping ammonia step (ii) (b).

34. The method of claim 33, wherein the fermenting in step (ii) and/or step (iv) further comprises fermenting by means of a bacterial population.

35. The method of claim 33, wherein the fermenting in step (ii) and/or step (iv) comprises fermenting anaerobically.

36. The method of claim 33, wherein the organic material provided in (i) comprises said animal material, wherein said organic material contains an amount of nitrogen (N) of more than 10% (w/v).

37. The method of claim 33, wherein the fermenting in step (ii) (a') is performed at a temperature of from 15° C. to less than 65° C.

38. The method of claim 33, wherein the fermenting in step (ii) (a') is performed at a temperature of from 25° C. to less than 55° C.

39. The method of claim 33, wherein the fermenting in step (ii) (a') is performed at a temperature of from 35° C. to less than 45° C.

40. The method of claim 33, wherein the fermenting in step (ii) (a') is performed for a period of time from 5 to less than 15 days.

41. The method of claim 33, wherein the fermenting in step (ii) (a') is performed for a period of time from 7 to less than 10 days.

42. The method of claim 6, wherein the organic material to be ensilaged comprises annual fodder crops.

43. The method of claim 1, wherein the fermenting comprises anaerobically fermenting in one or more biogas fermenters the processed organic material with biogas-producing microbial fermentation organisms.

44. The method of claim 43, wherein in step (iv) the fermenting comprises producing biogas in two biogas fermenters by anaerobic bacterial fermentation of the organic material, comprising:
   a. fermenting the processed organic material at a temperature above 45° C. with biogas-producing fermentation bacteria in a first biogas fermenter;
   b. diverting the fermented processed organic material to a second biogas fermenter; and then c. fermenting the diverted processed organic material with biogas-producing bacteria at a temperature below 45° C.

45. The method of claim 44, wherein the temperature in said first biogas fermenter is from 45° C. to 75° C.

46. The method of claim 44, wherein the temperature in said first biogas fermenter is from 55° C. to 60° C.

47. The method of claim 44, wherein the temperature in said second biogas fermenter is from 20° C. to 45° C.

48. The method of claim 44, wherein the temperature in said second biogas fermenter is from 30° C. to 35° C.

49. The method of claim 44, wherein the fermentation reaction in said first biogas fermenter is performed for 5 to 15 days.

50. The method of claim 44, wherein the fermentation reaction in said first biogas fermenter is performed for 7 to 10 days.

51. The method of claim 44, wherein the fermentation reaction in said second biogas fermenter is performed for 5 to 15 days.

52. The method of claim 44, wherein the fermentation reaction in said second biogas fermenter is performed for 7 to 10 days.

53. The method of claim 44, further comprising adding at least one anti-foaming agent, selected from the group consisting of polymers, plant oils, and salts, in an amount effective to reduce or eliminate foam formation in said fermenting step (iv).

54. The method of claim 53, wherein the plant oils comprise rape oil.

55. The method of claim 43, wherein the fermenting in step (iv) further comprises adding calcium ions to the organic material thereby flocculating substances and particles during biogas production, said calcium ions being capable of forming particulate, flock-forming calcium bridges therein.

56. The method of claim 55, the adding of the calcium-ions further results in the precipitation of orthophosphates, including dissolved $(PO_4)^{3-}$.

57. The method of claim 1, further comprising directing the obtained biogas to a gas engine capable of producing heat therefrom, wherein the heat produced by the gas engine is used to provide heat in the lime pressure cooking, the ammonia stripping, the fermenting, or a combination thereof.

58. The method of claim 1 wherein the microbial organisms and infectious agents include *Campylobacter, Salmonella, Yersinia, Ascaris*, vira or viroids.

59. The method of claim 1 further comprising the step of producing a nitrogen-comprising fertiliser (N fertiliser) containing ammonia, said production comprising the steps of
   i) collecting the ammonia stripped from the organic material in the stripping ammonia step, (ii) (b),
   ii) absorbing said collected ammonia in water or an acidic solution comprising sulphuric acid, and
   iii) obtaining the N-fertiliser containing said ammonia.

60. The method of claim 1 further comprising the step of producing phosphorus-comprising fertiliser (P-fertiliser), said production comprising the steps of
   i) diverting a slurry comprising the fermented organic material from said one or more biogas fermenters to a first separator,
   ii) separating said slurry into a solid fraction and a liquid fraction of reject water,
   iii) obtaining said solid fraction containing part of the phosphorus as calcium phosphate $(Ca_3(PO_4)_2)$ and organic phosphates initially suspended in the slurry, wherein said solid fraction is capable of being used as a P-fertiliser.

61. The method of claim 60, wherein the separator is a decanter centrifuge.

62. The method of claim 60, further comprising drying the solid fraction comprising phosphorus to produce a granulate comprising a P-fertiliser.

63. The method of claim 60, wherein the reject water obtained from the separation step has a content of nitrogen (N) and phosphorus (P) of less than 0.1% (w/v).

64. The method of claim 63, further comprising diverting the reject water to the stripping ammonia step and re-using said reject water for stripping ammonia from organic material.

65. The method of claim 63, wherein reject water is reusable for cleaning a stable.

66. The method of claim 63, wherein the reject water is free from sources capable of spreading zoonoses, veterinary vira, infectious bacteria, parasites, ESE prions and other prions.

67. The method of claim 60 comprising the further steps of stripping the ammonia from said reject water in a steam stripper.

68. The method of claim 67, further comprising condensing the stripped ammonia in a two step condensator.

69. The method of claim 68, wherein ammonia is condensed in a first step in a counter current of cooled ammonia condensate.

70. The method of claim 69, wherein ammonia not condensed in the first step is condensed in a counter current of permeate from a reverse osmosis step used for extracting potassium (K) from the reject water.

71. The method of claim 67 comprising the further step of diverting the stripped ammonia to the column on which ammonia from the first ammonia stripper tank is absorbed.

72. The method of claim 60 comprising the further step of producing a potassium-comprising fertiliser (K-fertiliser) from the organic material, said production comprising
   i) diverting the potassium-comprising liquid fraction of reject water from the first separation step to a second separation step,
   ii) separating the remaining organic and inorganic composition from the liquid fraction, and
   iii) obtaining a liquid concentrate comprising potassium, wherein said liquid concentrate comprising potassium is capable of being used as a K-fertiliser.

73. The method of claim 72, wherein the second separation step comprises subjecting the potassium-comprising liquid fraction through a micro filter operating with an intermittent aeration and filtration of the reject water, wherein said aeration provides decomposition of the remaining organic material and settling of inorganic flocks.

74. The method of claim 1, wherein, in step (iii) the processed organic material directed to the biogas fermenter is a slurry comprising the hydrolysed solid parts and a liquid.

75. The method of claim 1 wherein the pressure cooking is at a temperature of between 120° C. and 220° C.

76. The method of claim 1 wherein the lime pressure cooking is at a temperature of at least 140° C., a pressure of at least 4 bar, and a pH of at least about 10.

77. The method of claim 76 wherein the lime pressure cooking is at a temperature of 140-180° C., a pressure of 4-8 bar, and a pH of about 10-12.

78. The method of claim 77 wherein the provided organic matter comprises BSE prions and wherein the BSE prions are at least partially hydrolyzed as a result of said lime pressure cooking.

79. The method of claim 78 wherein, as a result of said stripping ammonia, the processed organic material diverted to said biogas fermenter has a lower ratio of nitrogen to carbon than did the organic material provided in step (i), and consequently the fermentation organisms in said one or more biogas fermenters fermenter produce additional extracellular proteinases and proteases capable of hydrolyzing the BSE prions than said fermentation organisms would if the ratio of nitrogen to carbon hadn't been reduced.

80. The method of claim 1 wherein the hydrolysis of cellulose, hemicellulose and/or lignin occurring in step (ii) (a) is substantially greater than that which would occur if that step were performed at 100° C.

81. The method of claim 1 wherein the production of biogas is substantially greater than that which would occur if step (ii) (a) were performed at 100° C.

82. The method of claim 1 wherein the organic material provided in step (i) comprises animal organic material.

83. The method of claim 82 wherein the animal organic material comprises manure.

84. The method of claim 1 wherein the temperature of the lime pressure cooking step (ii) (a) is less than that which causes substantial pyrolysis of the organic material to produce gases and polycyclic-aromatic hydrocarbons (PAH).

85. The method of claim 1 wherein said solid parts of the organic material provided in step (i) comprise cellulose and/or hemicellulose and/or lignin.

86. The method of claim 1 wherein at least some orthophosphate dissolved in said organic material is precipitated during said lime pressure cooking step (ii) (a).

87. The method of claim 1, wherein the stripping ammonia temperature is above 50° C.

88. The method of claim 1, wherein the stripping ammonia temperature is above 60° C.

89. The method of claim 1, wherein the operation time of the stripping ammonia step (ii) (b) is from 2 to 15 days.

90. The method of claim 1, wherein the operation time of the stripping ammonia step (ii) (b) is from 4 to 10 days.

91. The method of claim 1, wherein the operation time of the stripping ammonia step (ii) (b) is from 6 to 8 days.

92. The method of claim 1, wherein the organic material of step (i) comprises a maximum of 500 (w/v) solid parts.

93. The method of claim 1, wherein the organic material of step (i) comprises a maximum of 30% (w/v) solid parts.

94. The method of claim 1, wherein the organic material of step (i) comprises a maximum of 10% (w/v) solid parts.

95. The method of claim 1, further comprising absorbing the stripped ammonia in a column and then storing said ammonia in a tank.

96. The method of claim 85, wherein the step (ii) (b) of stripping ammonia is performed at a pH value above 9 and a temperature above 40° C.

97. The method of claim 96, wherein the pH value in the stripping ammonia step (ii) (b) is above 10.

98. The method of claim 96, wherein the pH value in the stripping ammonia step (ii) (b) is above 11.

99. The method of claim 1, wherein the operation time of the stripping ammonia step (ii) (b) is from 4 to 10 days.

100. The method of claim 1, wherein the operation time of the stripping ammonia step (ii) (b) is from 6 to 8 days.

101. The method of claim 1, wherein the organic material of step (i) comprises a maximum of 50% (w/v) solid parts.

102. The method of claim 85, wherein the step (ii) (a) of lime pressure cooking the organic material is performed at a temperature of from 120° C. to 220° C., at a pressure of 2 to 20 bar, with addition of lime sufficient to reach a pH value of from above 9 up to 12, and with an operation time of the step of lime pressure cooking of from at least 1 minute to less than 60 minutes.

103. The method of claim 102, wherein, in the lime pressure cooking step a), the temperature is in the interval of 180° C. to 200° C., wherein the pressure is from 10 bar to less than 16 bar, wherein the pH level is from 10 to 12, and wherein the operation time of the step of lime pressure cooking is from 5 minutes to 10 minutes.

104. The method of claim 102, wherein the provided organic material has a content of fibres of more than 10% (w/w).

105. The method of claim 85 wherein the lime pressure cooking step (ii) (a) is at a temperature of between 120° C. and 220° C.

106. The method of claim 85 wherein the lime pressure cooking step (ii) (a) is at a temperature of at least 140° C., a pressure of at least 4 bar, and a pH of at least about 10.

107. The method of claim 85 wherein the lime pressure cooking step (ii) (a) is at a temperature of 140-180° C., a pressure of 4-8 bar, and a pH of about 10-12.

* * * * *